United States Patent [19]
Xu et al.

[11] Patent Number: 6,066,467
[45] Date of Patent: May 23, 2000

[54] HIGH SPECIFICITY HOMOCYSTEINE ASSAYS FOR BIOLOGICAL SAMPLES

[75] Inventors: Mingxu Xu; Yuying Tan; Qinghong Han; Li Tang, all of San Diego, Calif.

[73] Assignee: AntiCancer, Inc., San Diego, Calif.

[21] Appl. No.: 09/340,991

[22] Filed: Jun. 28, 1999

Related U.S. Application Data

[63] Continuation-in-part of application No. 09/122,129, Jul. 24, 1998, which is a continuation-in-part of application No. 09/061,337, Apr. 17, 1998, which is a continuation-in-part of application No. 08/974,609, Nov. 19, 1997, which is a continuation-in-part of application No. 08/941,921, Oct. 1, 1997, abandoned, which is a continuation-in-part of application No. 08/918,214, Aug. 25, 1997, abandoned, which is a continuation-in-part of application No. 08/899,776, Jul. 24, 1997, abandoned.

[51] Int. Cl.[7] ................. C12Q 1/37; C12Q 1/00
[52] U.S. Cl. .................. 435/23; 435/4; 435/975
[58] Field of Search ................... 435/23, 4, 975

[56] References Cited

U.S. PATENT DOCUMENTS

| | | | |
|---|---|---|---|
| 4,940,658 | 7/1990 | Allen et al. | 435/23 |
| 5,438,017 | 8/1995 | Allen et al. | 435/23 |
| 5,478,729 | 12/1995 | Van Atta et al. | 435/23 |
| 5,631,127 | 5/1997 | Sundrehagen | 435/23 |
| 5,827,645 | 10/1998 | Sundrehagen et al. | 435/23 |
| 5,985,540 | 11/1999 | Tan et al. | 435/4 |

FOREIGN PATENT DOCUMENTS

| | | |
|---|---|---|
| WO 93/15220 | 8/1993 | WIPO . |
| WO 98/07872 | 2/1998 | WIPO . |
| WO 98/14562 | 4/1998 | WIPO . |

OTHER PUBLICATIONS

Araki, A. et al., *Journal of Chromatography* (1987) 422 : 43–52. Month not available.

Bagnara, A.S. et al., *Molecular and Biochemical Parasitology* (1996) 81 : 1–11. Month not available.

Dudman, N.P.B. et al., *Clinical Chemistry* (1996) 42 (12) : 2028–2032. Month not available.

Esaki, N. et al., "L–Methionine gamma–Lyase from *Pseudomonas putida* and Aeromonas " in *Methods in Enzymology* (1987) 143 : 459–465. Month not available.

Gage, D.A. et al., *Nature* (1997) 387 : 891–893. Month not available.

Garg, U.C., *Clinical Chemistry* (1997) 43(1) : 141–145. Month not available.

Gilfix, B.M. et al., *Clinical Chemistry* (1997) 43(4) : 687–688. Month not available.

(List continued on next page.)

*Primary Examiner*— Louise N. Leary
*Attorney, Agent, or Firm*—Morrison & Foerster LLP

[57] ABSTRACT

Novel enzymatic methods to determine the concentration of homocysteine in biological fluids are described. In a typical embodiment of the invention, the biological fluid sample is from a patient, and the methods of the invention are useful to assess risk for cardiovascular disease. The novel methods of the invention involve use of particular homocysteinase enzymes that permit the determination of homocysteine concentrations in biological samples without interference from the concentrations of cysteine and/or of methionine that are routinely present in such samples. There is also provided a diagnostic kit for use in determining the amount of homocysteine in a biological sample comprising (a) a homocysteinase having the aforementioned characteristics, and (b) at least one reagent capable of being used to determine the amount of product formed in the homocysteinase reaction. In a further aspect, the homocysteinase is provided as a chimeric molecule that comprises amino acid subsequences derived from, or patterned on, more than one homocysteinase, and which is typically produced from a chimeric polynucleotide that encodes therefor. Additional enhancements in homocysteine assay methodology include use of the enzyme γ-glutamylcysteine synthetase to further limit any interference from cysteine present in the biological samples.

19 Claims, 7 Drawing Sheets

```
AC2-1                                           Met His His His His His His
MGL1                                            --- --- --- --- --- --- ---
                                                 -7                       -5
AC2-1   Met Ser His Glu Arg Met Thr Pro Ala Thr Ala Cys Ile His Ala Asn
MGL1    Met Ser His Glu Arg Met Thr Pro Ala Thr Ala Cys Ile His Ala Asn
         1               5                  10                  15
AC2-1   Pro Gln Lys Asp Gln Phe Gly Ala Ala Ile Pro Pro Ile Tyr Gln Thr
MGL1    Pro Gln Lys Asp Gln Phe Gly Ala Ala Ile Pro Pro Ile Tyr Gln Thr
                        20                  25                  30
AC2-1   Ser Thr Phe Val Phe Asp Asn Cys Gln Gln Gly Gly Asn Arg Leu Ala
MGL1    Ser Thr Phe Val Phe Asp Asn Cys Gln Gln Gly Gly Asn Arg Phe Ala
                35                  40                  45
AC2-1   Gly Gln Glu Ser Gly Tyr Ile Tyr Thr Arg Leu Gly Asn Pro Thr Val
MGL1    Gly Gln Glu Ser Gly Tyr Ile Tyr Thr Arg Leu Gly Asn Pro Thr Val
            50                  55                  60
AC2-1   Ser Asn Leu Glu Gly Lys Ile Ala Phe Leu Glu Lys Thr Glu Ala Cys
MGL1    Ser Asn Leu Glu Gly Lys Ile Ala Phe Leu Glu Lys Thr Glu Ala Cys
        65                  70                  75                  80
AC2-1   Val Ala Thr Ser Ser Gly Met Gly Ala Ile Ala Ala Thr Val Leu Thr
MGL1    Val Ala Thr Ser Ser Gly Met Gly Ala Ile Ala Ala Thr Val Leu Thr
                85                  90                  95
AC2-1   Ile Leu Lys Ala Gly Asp His Leu Ile Ser Asp Glu Cys Leu Tyr Gly
MGL1    Ile Leu Lys Ala Gly Asp His Leu Ile Ser Asp Glu Cys Leu Tyr Gly
                    100                 105                 110
AC2-1   Cys Thr His Ala Leu Phe Glu His His Ala Leu Thr Lys Phe Gly Ile Gln
MGL1    Cys Thr His Ala Leu Phe Glu His His Ala Leu Thr Lys Phe Gly Ile Gln
                115                 120                 125
AC2-1   Val Asp Phe Ile Asn Thr Ala Ile Pro Gly Glu Val Lys Lys His Met
MGL1    Val Asp Phe Ile Asn Thr Ala Ile Pro Gly Glu Val Lys Lys His Met
                130                 135                 140
AC2-1   Lys Pro Asn Thr Lys Ile Val Tyr Phe Glu Thr Pro Ala Asn Pro Thr
MGL1    Lys Pro Asn Thr Lys Ile Val Tyr Phe Glu Thr Pro Ala Asn Pro Thr
        145                 150                 155                 160
AC2-1   Leu Lys Ile Ile Asp Met Glu Arg Val Cys Lys Glu Ala His Ser Gln
MGL1    Leu Lys Ile Ile Asp Met Glu Arg Val Cys Lys Asp Ala His Ser Gln
                    165                 170                 175
AC2-1   Glu Gly Val Leu Val Ile Ala Asp Asn Thr Phe Cys Ser Pro Met Ile
MGL1    Glu Gly Val Leu Val Ile Ala Asp Asn Thr Phe Cys Ser Pro Met Ile
                180                 185                 190
```

OTHER PUBLICATIONS

Hoffman, R.M. et al., "Diagnosis and treatment of homocysteine disease using recombinant homocysteinase". 2nd International Conference on Homocysteine Metabolism, Nijmegen, Netherlands, Apr. 26–29, 1998. Netherlands Journal of Medicine 52 (Suppl) 1998. S41. ISSN: 0300–2977, XP002087823. Month not available.

Hori, H. et al., *Cancer Research* (1996) 56 : 2116–2122. Month not available.

Inoue, Y. et al., *Applied Microbiology and Biotechnology* (1993) 38 : 473–477. Month not available.

Ito, S. et al., *Journal of Biochemistry* (1976) 79 : 1263–1272. Month not available.

Jakubowsky, H. et al., *FEBS Letters* (1993) 317(3) : 237–240. Month not available.

Kang, S. et al., *Annual Review of Nutrition* (1992) 12 : 279–298. Month not avialable.

Kerr. R.A. *Science* (1997) 276 : 703–704. Month not available.

Lockwood, B. et al., *Biochemical Journal* (1991) 279 : 675–682. Month not available.

Markos, A. et al., *FEMS Microbiology Letters* (1996) 135 : 259–264. Month not available.

McCully, K.S., *American Journal of Pathology* (1996) 56: 111–128. Month not available.

McCully, K.S., *Annals of Clinical and Laboratory Science* (1993) 23(6) : 477–493. Month not available.

McCully, K.S., *Annals of Clinical and Laboratory Science* (1994) 24(1) : 27–59. Month not available.

McCully, K.S., *Annals of Clinical and Laboratory Science* (1994) 24(2) : 134–152. Month not available.

McCully, K.S., *Nature Medicine* (1996) 2(4) : 386–389. Month not available.

McKie, A. et al., *Journal of Biological Chemistry* (1998) 273 : 5549–5556. Month not available.

Mottram, J.C., *Gene Bank,* (Jul. 17, 1997), Accession No. AJ000486, NID g2330884; and Accession No. AJ000487, NID g2330886. Month not available.

Mudd, S.H. et al., *American Journal of Human Genetics* (1985) 37 : 1–31. Month not available.

Nygard, O. et al., *The New England Journal of Medicine* (1997) 337(4) : 230–236. Month not available.

Pennist, E., *Science* (1997) 276 : 705–706. Month not available.

Riley, D.E. et al., *Molecular and Biochemical Parasitology* (1992) 51 : 161–164. Month not available.

Robinson, K. et al., *Cleveland ClinicJournal of Medicine,* (1994) 6 : 438–450. Month not available.

Selhub, J. et al., *New England Journal. of Medicine* (1995) 332 : 286–291. Month not available.

Shipchandler, M.T. et al., *Clinical Chemistry* (1995) 41(7) : 991–994. Month not available.

Stampfer, M. et al, *Journal of the American Medical Association* (1992) 268 : 877–881. Month not available.

Tan, Y. et al., *Protein Expression and Purification* (1997) 9 : 233–245.

Tanaka, H. et al., *Journal of Applied Biochemistry* (1980) 2 : 439–444.

Tanaka, H. et al., *Biochemistry* (1977) 16 : 100–106. Month not available.

Thong, K–W. et al., *Experimental Parasitology* (1987) 63 : 143–151. Month not available.

Thong, K–W. et al., *IRCS Journal of Medical Science* (1985) 13 : 493–494. Month not available.

Thong, K–W. et al., *IRCS Journal of Medical Science* (1985) 13 : 495–496. Month not available.

Thong, K–W. et al., *Molecular and Biochemical Parasitology* (1987) 23 : 223–231. Month not available.

Ueland, P. et al., "Plasma Homocysteine and Cardiovascular Disease", in *Atherosclerotic Cardiovascular Disease, Hemostasis and Endothelial Function,* Francis, R.B. Jr., ed., 1992, pp. 183–236, Marcel Dekker, Inc, New York. Month not available.

Vilaseca, M.A. et al., *Clinical Chemistry* (1997) 43(4) : 690–691. Month not available.

Watanabe, K. et al., *Nucleic Acids Research* (1986) 14 : 4393–4400. Month not available.

Wolfe, G.V. et al., *Nature* (1997) 387 : 894–897. Month not available.

Yamaguchi, A. et al., *Annual Report of Sapporo City Institute of Public Health* (1993) 20 : 67–74. Month not available.

Zuo, X. et al., *Microbiology* (1995) 141 : 2637–2642. Month not available.

```
AC2-1                                         Met His His His His His His
MGL1                                          --- --- --- --- --- --- ---
                                               -7          -5
AC2-1  Met Ser His Glu Arg Met Thr Pro Ala Thr Ala Cys Ile His Ala Asn
MGL1   Met Ser His Glu Arg Met Thr Pro Ala Thr Ala Cys Ile His Ala Asn
         1           5              10                      15
AC2-1  Pro Gln Lys Asp Gln Phe Gly Ala Ala Ile Pro Pro Ile Tyr Gln Thr
MGL1   Pro Gln Lys Asp Gln Phe Gly Ala Ala Ile Pro Pro Ile Tyr Gln Thr
                    20              25                      30
AC2-1  Ser Thr Phe Val Phe Asp Asn Cys Gln Gln Gly Gly Asn Arg Leu Ala
MGL1   Ser Thr Phe Val Phe Asp Asn Cys Gln Gln Gly Gly Asn Arg Phe Ala
                    35              40                      45
AC2-1  Gly Gln Glu Ser Gly Tyr Ile Tyr Thr Arg Leu Gly Asn Pro Thr Val
MGL1   Gly Gln Glu Ser Gly Tyr Ile Tyr Thr Arg Leu Gly Asn Pro Thr Val
             50              55                      60
AC2-1  Ser Asn Leu Glu Gly Lys Ile Ala Phe Leu Glu Lys Thr Glu Ala Cys
MGL1   Ser Asn Leu Glu Gly Lys Ile Ala Phe Leu Glu Lys Thr Glu Ala Cys
         65              70                      75                  80
AC2-1  Val Ala Thr Ser Ser Gly Met Gly Ala Ile Ala Ala Thr Val Leu Thr
MGL1   Val Ala Thr Ser Ser Gly Met Gly Ala Ile Ala Ala Thr Val Leu Thr
                    85              90                      95
AC2-1  Ile Leu Lys Ala Gly Asp His Leu Ile Ser Asp Glu Cys Leu Tyr Gly
MGL1   Ile Leu Lys Ala Gly Asp His Leu Ile Ser Asp Glu Cys Leu Tyr Gly
                   100             105                     110
AC2-1  Cys Thr His Ala Leu Phe Glu His Ala Leu Thr Lys Phe Gly Ile Gln
MGL1   Cys Thr His Ala Leu Phe Glu His Ala Leu Thr Lys Phe Gly Ile Gln
                   115             120                     125
AC2-1  Val Asp Phe Ile Asn Thr Ala Ile Pro Gly Glu Val Lys Lys His Met
MGL1   Val Asp Phe Ile Asn Thr Ala Ile Pro Gly Glu Val Lys Lys His Met
                   130             135                     140
AC2-1  Lys Pro Asn Thr Lys Ile Val Tyr Phe Glu Thr Pro Ala Asn Pro Thr
MGL1   Lys Pro Asn Thr Lys Ile Val Tyr Phe Glu Thr Pro Ala Asn Pro Thr
        145             150                     155                 160
AC2-1  Leu Lys Ile Ile Asp Met Glu Arg Val Cys Lys Glu Ala His Ser Gln
MGL1   Leu Lys Ile Ile Asp Met Glu Arg Val Cys Lys Asp Ala His Ser Gln
                   165             170                     175
AC2-1  Glu Gly Val Leu Val Ile Ala Asp Asn Thr Phe Cys Ser Pro Met Ile
MGL1   Glu Gly Val Leu Val Ile Ala Asp Asn Thr Phe Cys Ser Pro Met Ile
                   180             185                     190
```

FIG. 1A

```
AC2-1  Thr Asn Pro Val Asp Phe Gly Val Asp Val Val Val His Ser Ala Thr
MGL1   Thr Asn Pro Val Asp Phe Gly Val Asp Val Val Val His Ser Ala Thr
               195                 200                 205
AC2-1  Lys Tyr Ile Asn Gly His Thr Asp Val Val Ala Gly Leu Ile Cys Gly
MGL1   Lys Tyr Ile Asn Gly His Thr Asp Val Val Ala Gly Leu Ile Cys Gly
           210                 215                 220
AC2-1  Lys Ala Asp Leu Leu Gln Gln Ile Arg Met Val Gly Ile Lys Asp Ile
MGL1   Lys Ala Asp Leu Leu Gln Gln Ile Arg Met Val Gly Ile Lys Asp Ile
           225                 230                 235                 240
AC2-1  Thr Gly Ser Val Ile Ser Pro His Asp Ala Trp Leu Ile Thr Arg Gly
MGL1   Thr Gly Ser Val Ile Ser Pro His Asp Ala Trp Leu Ile Thr Arg Gly
                   245                 250                 255
AC2-1  Leu Ser Thr Leu Asn Ile Arg Met Lys Ala Glu Ser Glu Asn Ala Met
MGL1   Leu Ser Thr Leu Asn Ile Arg Met Lys Ala Glu Ser Glu Asn Ala Met
                   260                 265                 270
AC2-1  Lys Val Ala Glu Tyr Leu Lys Ser His Pro Ala Val Glu Lys Val Tyr
MGL1   Lys Val Ala Glu Tyr Leu Lys Ser His Pro Ala Val Glu Lys Val Tyr
               275                 280                 285
AC2-1  Tyr Pro Gly Phe Glu Asp His Glu Gly His Asp Ile Ala Lys Lys Gln
MGL1   Tyr Pro Gly Phe Glu Asp His Glu Gly His Asp Ile Ala Lys Lys Gln
               290                 295                 300
AC2-1  Met Arg Met Tyr Gly Ser Met Ile Thr Phe Ile Leu Lys Ser Gly Phe
MGL1   Met Arg Met Ser Gly Ser Met Ile Thr Phe Ile Leu Lys Ser Gly Phe
           305                 310                 315                 320
AC2-1  Glu Gly Ala Lys Lys Leu Leu Asp Asn Leu Lys Leu Ile Thr Leu Ala
MGL1   Glu Gly Ala Lys Lys Leu Leu Asp Asn Leu Lys Leu Ile Thr Leu Ala
                   325                 330                 335
AC2-1  Val Ser Leu Gly Gly Cys Glu Ser Leu Ile Gln His Pro Ala Ser Met
MGL1   Val Ser Leu Gly Gly Cys Glu Ser Leu Ile Gln His Pro Ala Ser Met
                   340                 345                 350
AC2-1  Thr His Ala Val Val Pro Lys Glu Glu Arg Glu Ala Ala Gly Ile Thr
MGL1   Thr His Ala Val Val Pro Lys Glu Glu Arg Glu Ala Ala Gly Ile Thr
                   355                 360                 365
AC2-1  Asp Gly Met Ile Arg Leu Ser Val Gly Ile Glu Asp Ala Asp Glu Leu
MGL1   Asp Gly Met Ile Arg Leu Ser Val Gly Ile Glu Asp Ala Asp Glu Leu
                   370                 375                 380
AC2-1  Ile Ala Asp Phe Lys Gln Gly Leu Asp Ala Leu Leu
MGL1   Ile Ala Asp Phe Lys Gln Gly Leu Asp Ala Leu Leu
                   385                 390                 395
```

FIG. 1B

| HCY Con.(μM) | 665/690 | Sample | 665/690 | μM Of HCY |
|---|---|---|---|---|
| 0 | 0 | | | |
| 5 | 2.86 | Dr. Hoffman's Serum | 3.71 | 7.259 |
| 10 | 5.21 | Dr. Hoffman's Finger Serum | 4.34 | 8.479 |
| 20 | 9.53 | | | |
| 40 | 20.93 | | | |

| CYS Con(μM) | HCY Con.(μM) | 665/690 |
|---|---|---|
| 0 | 0 | 0 |
| 200 | 5 | 2.27 |
| 200 | 10 | 4.89 |
| 200 | 20 | 12.01 |
| 200 | 40 | 19.37 |

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:1:

Cys Ser Arg Ala Asp Ile Ile Ala Lys Val Lys Ser
1             5                    10

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:2:

Val Gly Ser Gln Ala Leu Val Asp Arg Ile Arg Leu
1               5                  10

(2) INFORMATION FOR SEQ ID NO:3:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:3:

Asp Val Asp
1

(2) INFORMATION FOR SEQ ID NO:4:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:4:

Glu Leu Lys
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:5:

Cys His Val Val
1

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:6:

Ala Leu Gln Leu
1

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:7:

Cys Glu Asn Val Gln Asp Ile Ile Asp Asp
1               5                  10

(2) INFORMATION FOR SEQ ID NO:8:

(i) SEQUENCE CHARACTERISTICS:

-continued (A) LENGTH: 10 amino acids
(B) TYPE: amino acid
(C) STRANDEDNESS: single
(D) TOPOLOGY: linear (xi) SEQUENCE DESCRIPTION: SEQ ID NO:8:

Gly Leu Glu Asp Ile Asp Asp Leu Leu Ala
1               5                   10

(2) INFORMATION FOR SEQ ID NO:9:

(i) SEQUENCE CHARACTERISTICS:
        (A) LENGTH: 1240 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 18..1226

(ix) FEATURE:
        (A) NAME/KEY: mat_peptide
        (B) LOCATION: 39

(xi) SEQUENCE DESCRIPTION: SEQ ID NO:9:

```
AAGAAGGAGA TATACAT ATG CAT CAT CAT CAT CAT CAC ATG TCT CAC GAG          50
                    Met His His His His His His Met Ser His Glu
                     -7          -5                    1

AGA ATG ACC CCA GCA ACA GCA TGC ATC CAT GCT AAT CCA CAG AAG GAT         98
Arg Met Thr Pro Ala Thr Ala Cys Ile His Ala Asn Pro Gln Lys Asp
 5              10                  15                  20

CAG TTT GGA GCA GCC ATC CCA CCA ATC TAC CAA ACA TCA ACA TTC GTT        146
Gln Phe Gly Ala Ala Ile Pro Pro Ile Tyr Gln Thr Ser Thr Phe Val
            25                  30                  35

TTC GAT AAC TGC CAA CAG GGT GGA AAC AGA CTC GCT GGT CAG GAA TCC        194
Phe Asp Asn Cys Gln Gln Gly Gly Asn Arg Leu Ala Gly Gln Glu Ser
                40                  45                  50

GGC TAC ATC TAC ACA CGT CTC GGC AAC CCA ACA GTT TCA AAC CTC GAA        242
Gly Tyr Ile Tyr Thr Arg Leu Gly Asn Pro Thr Val Ser Asn Leu Glu
        55                  60                  65

GGC AAG ATC GCC TTC CTC GAG AAA ACA GAA GCA TGC GTT GCC ACA TCT        290
Gly Lys Ile Ala Phe Leu Glu Lys Thr Glu Ala Cys Val Ala Thr Ser
    70                  75                  80

TCT GGC ATG GGT GCC ATT GCT GCT ACA GTT TTG ACA ATC CTC AAG GCC        338
Ser Gly Met Gly Ala Ile Ala Ala Thr Val Leu Thr Ile Leu Lys Ala
85                  90                  95                 100

GGA GAT CAC TTA ATC TCC GAT GAG TGC CTT TAT GGC TGC ACA CAT GCT        386
Gly Asp His Leu Ile Ser Asp Glu Cys Leu Tyr Gly Cys Thr His Ala
                105                 110                 115

CTC TTT GAG CAC GCA TTG ACA AAG TTC GGC ATC CAG GTC GAC TTC ATC        434
Leu Phe Glu His Ala Leu Thr Lys Phe Gly Ile Gln Val Asp Phe Ile
            120                 125                 130

AAC ACA GCC ATC CCA GGC GAG GTC AAG AAG CAC ATG AAG CCA AAC ACA        482
Asn Thr Ala Ile Pro Gly Glu Val Lys Lys His Met Lys Pro Asn Thr
        135                 140                 145

AAG ATT GTC TAT TTC GAG ACA CCA GCC AAC CCA ACA CTC AAG ATC ATC        530
Lys Ile Val Tyr Phe Glu Thr Pro Ala Asn Pro Thr Leu Lys Ile Ile
    150                 155                 160

GAC ATG GAG CGC GTC TGC AAG GAA GCC CAC AGC CAG GAG GGC GTC TTA        578
Asp Met Glu Arg Val Cys Lys Glu Ala His Ser Gln Glu Gly Val Leu
165                 170                 175                 180

GTT ATC GCC GAT AAC ACA TTC TGC TCA CCA ATG ATC ACA AAC CCA GTC        626
Val Ile Ala Asp Asn Thr Phe Cys Ser Pro Met Ile Thr Asn Pro Val
```

-continued

```
              185                 190                 195
GAC TTT GGC GTC GAT GTT GTT GTC CAC TCT GCA ACA AAG TAC ATC AAC      674
Asp Phe Gly Val Asp Val Val Val His Ser Ala Thr Lys Tyr Ile Asn
            200                 205                 210

GGC CAC ACA GAT GTC GTC GCT GGC CTT ATC TGT GGC AAG GCT GAC CTC      722
Gly His Thr Asp Val Val Ala Gly Leu Ile Cys Gly Lys Ala Asp Leu
            215                 220                 225

CTT CAA CAG ATT CGT ATG GTT GGT ATC AAG GAT ATC ACA GGA TCT GTT      770
Leu Gln Gln Ile Arg Met Val Gly Ile Lys Asp Ile Thr Gly Ser Val
        230                 235                 240

ATC AGC CCA CAC GAC GCT TGG CTC ATC ACA CGT GGC CTC TCA ACA CTC      818
Ile Ser Pro His Asp Ala Trp Leu Ile Thr Arg Gly Leu Ser Thr Leu
245                 250                 255                 260

AAC ATC AGA ATG AAG GCT GAG AGC GAG AAC GCC ATG AAG GTC GCT GAG      866
Asn Ile Arg Met Lys Ala Glu Ser Glu Asn Ala Met Lys Val Ala Glu
                265                 270                 275

TAC CTC AAA TCT CAC CCA GCC GTT GAG AAG GTT TAC TAC CCA GGC TTC      914
Tyr Leu Lys Ser His Pro Ala Val Glu Lys Val Tyr Tyr Pro Gly Phe
                280                 285                 290

GAG GAC CAC GAG GGC CAC GAT ATC GCT AAG AAG CAG ATG AGA ATG TAC      962
Glu Asp His Glu Gly His Asp Ile Ala Lys Lys Gln Met Arg Met Tyr
                295                 300                 305

GGT TCA ATG ATC ACA TTC ATC CTC AAG TCC GGC TTC GAA GGC GCT AAG     1010
Gly Ser Met Ile Thr Phe Ile Leu Lys Ser Gly Phe Glu Gly Ala Lys
310                 315                 320

AAG CTC CTC GAC AAC CTC AAG CTT ATC ACA CTT GCA GTT TCC CTT GGT     1058
Lys Leu Leu Asp Asn Leu Lys Leu Ile Thr Leu Ala Val Ser Leu Gly
325                 330                 335                 340

GGC TGC GAG TCC CTC ATC CAG CAC CCA GCT TCA ATG ACT CAC GCT GTC     1106
Gly Cys Glu Ser Leu Ile Gln His Pro Ala Ser Met Thr His Ala Val
                345                 350                 355

GTT CCA AAG GAG GAG CGT GAG GCC GCT GGT ATT ACA GAT GGC ATG ATC     1154
Val Pro Lys Glu Glu Arg Glu Ala Ala Gly Ile Thr Asp Gly Met Ile
                360                 365                 370

CGC CTT TCT GTC GGT ATT GAA GAT GCC GAC GAA CTC ATC GCT GAT TTC     1202
Arg Leu Ser Val Gly Ile Glu Asp Ala Asp Glu Leu Ile Ala Asp Phe
            375                 380                 385

AAA CAG GGC CTT GAC GCT CTT TTA TAAGGATCCT CTAG                     1240
Lys Gln Gly Leu Asp Ala Leu Leu
390                 395
```

(2) INFORMATION FOR SEQ ID NO:10:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:10:

```
Met His His His His His Met Ser His Glu Arg Met Thr Pro Ala
 -7          -5                    1                   5

Thr Ala Cys Ile His Ala Asn Pro Gln Lys Asp Gln Phe Gly Ala Ala
        10                  15                  20                  25

Ile Pro Pro Ile Tyr Gln Thr Ser Thr Phe Val Phe Asp Asn Cys Gln
                    30                  35                  40

Gln Gly Gly Asn Arg Leu Ala Gly Gln Glu Ser Gly Tyr Ile Tyr Thr
                45                  50                  55

Arg Leu Gly Asn Pro Thr Val Ser Asn Leu Glu Gly Lys Ile Ala Phe
```

-continued

```
              60                  65                  70
Leu Glu Lys Thr Glu Ala Cys Val Ala Thr Ser Ser Gly Met Gly Ala
         75                  80                  85
Ile Ala Ala Thr Val Leu Thr Ile Leu Lys Ala Gly Asp His Leu Ile
 90                  95                 100                 105
Ser Asp Glu Cys Leu Tyr Gly Cys Thr His Ala Leu Phe Glu His Ala
                110                 115                 120
Leu Thr Lys Phe Gly Ile Gln Val Asp Phe Ile Asn Thr Ala Ile Pro
            125                 130                 135
Gly Glu Val Lys Lys His Met Lys Pro Asn Thr Lys Ile Val Tyr Phe
            140                 145                 150
Glu Thr Pro Ala Asn Pro Thr Leu Lys Ile Ile Asp Met Glu Arg Val
155                 160                 165
Cys Lys Glu Ala His Ser Gln Glu Gly Val Leu Val Ile Ala Asp Asn
170                 175                 180                 185
Thr Phe Cys Ser Pro Met Ile Thr Asn Pro Val Asp Phe Gly Val Asp
                190                 195                 200
Val Val Val His Ser Ala Thr Lys Tyr Ile Asn Gly His Thr Asp Val
            205                 210                 215
Val Ala Gly Leu Ile Cys Gly Lys Ala Asp Leu Leu Gln Gln Ile Arg
            220                 225                 230
Met Val Gly Ile Lys Asp Ile Thr Gly Ser Val Ile Ser Pro His Asp
235                 240                 245
Ala Trp Leu Ile Thr Arg Gly Leu Ser Thr Leu Asn Ile Arg Met Lys
250                 255                 260                 265
Ala Glu Ser Glu Asn Ala Met Lys Val Ala Glu Tyr Leu Lys Ser His
                270                 275                 280
Pro Ala Val Glu Lys Val Tyr Tyr Pro Gly Phe Glu Asp His Glu Gly
            285                 290                 295
His Asp Ile Ala Lys Lys Gln Met Arg Met Tyr Gly Ser Met Ile Thr
            300                 305                 310
Phe Ile Leu Lys Ser Gly Phe Glu Gly Ala Lys Lys Leu Leu Asp Asn
315                 320                 325
Leu Lys Leu Ile Thr Leu Ala Val Ser Leu Gly Gly Cys Glu Ser Leu
330                 335                 340                 345
Ile Gln His Pro Ala Ser Met Thr His Ala Val Val Pro Lys Glu Glu
                350                 355                 360
Arg Glu Ala Ala Gly Ile Thr Asp Gly Met Ile Arg Leu Ser Val Gly
            365                 370                 375
Ile Glu Asp Ala Asp Glu Leu Ile Ala Asp Phe Lys Gln Gly Leu Asp
            380                 385                 390
Ala Leu Leu
    395
```

(2) INFORMATION FOR SEQ ID NO:11:

(i) SEQUENCE CHARACTERISTICS:
        (A) LENGTH: 1191 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..1188
        (D) OTHER INFORMATION: /codon_start= 1

(ix) FEATURE:
    (A) NAME/KEY: mat_peptide
    (B) LOCATION: 1

(xi) SEQUENCE DESCRIPTION: SEQ ID NO:11:

| | | | | | | | | | | | | | | | | |
|---|---|---|---|---|---|---|---|---|---|---|---|---|---|---|---|---|
| ATG | TCT | CAC | GAG | AGA | ATG | ACC | CCA | GCA | ACA | GCA | TGC | ATC | CAT | GCT | AAT | 48 |
| Met | Ser | His | Glu | Arg | Met | Thr | Pro | Ala | Thr | Ala | Cys | Ile | His | Ala | Asn | |
| 1 | | | | 5 | | | | | 10 | | | | | 15 | | |
| CCA | CAG | AAG | GAT | CAG | TTT | GGA | GCA | GCC | ATC | CCA | CCA | ATC | TAC | CAA | ACA | 96 |
| Pro | Gln | Lys | Asp | Gln | Phe | Gly | Ala | Ala | Ile | Pro | Pro | Ile | Tyr | Gln | Thr | |
| | | | 20 | | | | | 25 | | | | | 30 | | | |
| TCA | ACA | TTC | GTT | TTC | GAT | AAC | TGC | CAA | CAG | GGT | GGA | AAC | AGA | TTC | GCT | 144 |
| Ser | Thr | Phe | Val | Phe | Asp | Asn | Cys | Gln | Gln | Gly | Gly | Asn | Arg | Phe | Ala | |
| | | 35 | | | | | 40 | | | | | 45 | | | | |
| GGT | CAG | GAA | TCC | GGC | TAC | ATC | TAC | ACA | CGT | CTC | GGC | AAC | CCA | ACA | GTT | 192 |
| Gly | Gln | Glu | Ser | Gly | Tyr | Ile | Tyr | Thr | Arg | Leu | Gly | Asn | Pro | Thr | Val | |
| | 50 | | | | | 55 | | | | | 60 | | | | | |
| TCA | AAC | CTC | GAA | GGC | AAG | ATC | GCC | TTC | CTC | GAG | AAA | ACA | GAA | GCA | TGC | 240 |
| Ser | Asn | Leu | Glu | Gly | Lys | Ile | Ala | Phe | Leu | Glu | Lys | Thr | Glu | Ala | Cys | |
| 65 | | | | | 70 | | | | | 75 | | | | | 80 | |
| GTT | GCC | ACA | TCT | TCT | GGC | ATG | GGT | GCC | ATT | GCT | GCT | ACA | GTT | TTG | ACA | 288 |
| Val | Ala | Thr | Ser | Ser | Gly | Met | Gly | Ala | Ile | Ala | Ala | Thr | Val | Leu | Thr | |
| | | | | 85 | | | | | 90 | | | | | 95 | | |
| ATC | CTC | AAG | GCC | GGA | GAT | CAC | TTA | ATC | TCC | GAT | GAG | TGC | CTT | TAT | GGC | 336 |
| Ile | Leu | Lys | Ala | Gly | Asp | His | Leu | Ile | Ser | Asp | Glu | Cys | Leu | Tyr | Gly | |
| | | | 100 | | | | | 105 | | | | | 110 | | | |
| TGC | ACA | CAT | GCT | CTC | TTT | GAG | CAC | GCA | TTG | ACA | AAG | TTC | GGC | ATC | CAG | 384 |
| Cys | Thr | His | Ala | Leu | Phe | Glu | His | Ala | Leu | Thr | Lys | Phe | Gly | Ile | Gln | |
| | | 115 | | | | | 120 | | | | | 125 | | | | |
| GTC | GAC | TTC | ATC | AAC | ACA | GCC | ATC | CCA | GGC | GAG | GTC | AAG | AAG | CAC | ATG | 432 |
| Val | Asp | Phe | Ile | Asn | Thr | Ala | Ile | Pro | Gly | Glu | Val | Lys | Lys | His | Met | |
| | 130 | | | | | 135 | | | | | 140 | | | | | |
| AAG | CCA | AAC | ACA | AAG | ATT | GTC | TAT | TTC | GAG | ACA | CCA | GCC | AAC | CCA | ACA | 480 |
| Lys | Pro | Asn | Thr | Lys | Ile | Val | Tyr | Phe | Glu | Thr | Pro | Ala | Asn | Pro | Thr | |
| 145 | | | | | 150 | | | | | 155 | | | | | 160 | |
| CTC | AAG | ATC | ATC | GAC | ATG | GAG | CGC | GTC | TGC | AAG | GAC | GCC | CAC | AGC | CAG | 528 |
| Leu | Lys | Ile | Ile | Asp | Met | Glu | Arg | Val | Cys | Lys | Asp | Ala | His | Ser | Gln | |
| | | | | 165 | | | | | 170 | | | | | 175 | | |
| GAG | GGC | GTC | TTA | GTT | ATC | GCC | GAT | AAC | ACA | TTC | TGC | TCA | CCA | ATG | ATC | 576 |
| Glu | Gly | Val | Leu | Val | Ile | Ala | Asp | Asn | Thr | Phe | Cys | Ser | Pro | Met | Ile | |
| | | | 180 | | | | | 185 | | | | | 190 | | | |
| ACA | AAC | CCA | GTC | GAC | TTT | GGC | GTC | GAT | GTT | GTT | GTC | CAC | TCT | GCA | ACA | 624 |
| Thr | Asn | Pro | Val | Asp | Phe | Gly | Val | Asp | Val | Val | Val | His | Ser | Ala | Thr | |
| | | 195 | | | | | 200 | | | | | 205 | | | | |
| AAG | TAC | ATC | AAC | GGC | CAC | ACA | GAT | GTC | GTC | GCT | GGC | CTT | ATC | TGT | GGC | 672 |
| Lys | Tyr | Ile | Asn | Gly | His | Thr | Asp | Val | Val | Ala | Gly | Leu | Ile | Cys | Gly | |
| | 210 | | | | | 215 | | | | | 220 | | | | | |
| AAG | GCT | GAC | CTC | CTT | CAA | CAG | ATT | CGT | ATG | GTT | GGT | ATC | AAG | GAT | ATC | 720 |
| Lys | Ala | Asp | Leu | Leu | Gln | Gln | Ile | Arg | Met | Val | Gly | Ile | Lys | Asp | Ile | |
| 225 | | | | | 230 | | | | | 235 | | | | | 240 | |
| ACA | GGA | TCT | GTT | ATC | AGC | CCA | CAC | GAC | GCT | TGG | CTC | ATC | ACA | CGT | GGC | 768 |
| Thr | Gly | Ser | Val | Ile | Ser | Pro | His | Asp | Ala | Trp | Leu | Ile | Thr | Arg | Gly | |
| | | | | 245 | | | | | 250 | | | | | 255 | | |
| CTC | TCA | ACA | CTC | AAC | ATC | AGA | ATG | AAG | GCT | GAG | AGC | GAG | AAC | GCC | ATG | 816 |
| Leu | Ser | Thr | Leu | Asn | Ile | Arg | Met | Lys | Ala | Glu | Ser | Glu | Asn | Ala | Met | |
| | | | 260 | | | | | 265 | | | | | 270 | | | |
| AAG | GTC | GCT | GAG | TAC | CTC | AAA | TCT | CAC | CCA | GCC | GTT | GAG | AAG | GTT | TAC | 864 |
| Lys | Val | Ala | Glu | Tyr | Leu | Lys | Ser | His | Pro | Ala | Val | Glu | Lys | Val | Tyr | |
| | | 275 | | | | | 280 | | | | | 285 | | | | |
| TAC | CCA | GGC | TTC | GAG | GAC | CAC | GAG | GGC | CAC | GAT | ATC | GCT | AAG | AAG | CAG | 912 |

```
Tyr Pro Gly Phe Glu Asp His Glu Gly His Asp Ile Ala Lys Lys Gln
            290                 295                 300

ATG AGA ATG TCG GGT TCA ATG ATC ACA TTC ATC CTC AAG TCC GGC TTC       960
Met Arg Met Ser Gly Ser Met Ile Thr Phe Ile Leu Lys Ser Gly Phe
305                 310                 315                 320

GAA GGC GCT AAG AAG CTC CTC GAC AAC CTC AAG CTT ATC ACA CTT GCA      1008
Glu Gly Ala Lys Lys Leu Leu Asp Asn Leu Lys Leu Ile Thr Leu Ala
                325                 330                 335

GTT TCC CTT GGT GGC TGC GAG TCC CTC ATC CAG CAC CCA GCT TCA ATG      1056
Val Ser Leu Gly Gly Cys Glu Ser Leu Ile Gln His Pro Ala Ser Met
            340                 345                 350

ACT CAC GCT GTC GTT CCA AAG GAG GAG CGT GAG GCC GCT GGT ATT ACA      1104
Thr His Ala Val Val Pro Lys Glu Glu Arg Glu Ala Ala Gly Ile Thr
355                 360                 365

GAT GGC ATG ATC CGC CTT TCT GTC GGT ATT GAA GAT GCC GAC GAA CTC      1152
Asp Gly Met Ile Arg Leu Ser Val Gly Ile Glu Asp Ala Asp Glu Leu
370                 375                 380

ATC GCT GAT TTC AAA CAG GGC CTT GAC GCT CTT TTA TAA                  1191
Ile Ala Asp Phe Lys Gln Gly Leu Asp Ala Leu Leu
385                 390                 395
```

(2) INFORMATION FOR SEQ ID NO:12:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser His Glu Arg Met Thr Pro Ala Thr Ala Cys Ile His Ala Asn
1               5                   10                  15

Pro Gln Lys Asp Gln Phe Gly Ala Ala Ile Pro Pro Ile Tyr Gln Thr
                20                  25                  30

Ser Thr Phe Val Phe Asp Asn Cys Gln Gln Gly Gly Asn Arg Phe Ala
            35                  40                  45

Gly Gln Glu Ser Gly Tyr Ile Tyr Thr Arg Leu Gly Asn Pro Thr Val
        50                  55                  60

Ser Asn Leu Glu Gly Lys Ile Ala Phe Leu Glu Lys Thr Glu Ala Cys
65                  70                  75                  80

Val Ala Thr Ser Ser Gly Met Gly Ala Ile Ala Thr Val Leu Thr
                85                  90                  95

Ile Leu Lys Ala Gly Asp His Leu Ile Ser Asp Glu Cys Leu Tyr Gly
                100                 105                 110

Cys Thr His Ala Leu Phe Glu His Ala Leu Thr Lys Phe Gly Ile Gln
            115                 120                 125

Val Asp Phe Ile Asn Thr Ala Ile Pro Gly Glu Val Lys Lys His Met
        130                 135                 140

Lys Pro Asn Thr Lys Ile Val Tyr Phe Glu Thr Pro Ala Asn Pro Thr
145                 150                 155                 160

Leu Lys Ile Ile Asp Met Glu Arg Val Cys Lys Asp Ala His Ser Gln
                165                 170                 175

Glu Gly Val Leu Val Ile Ala Asp Asn Thr Phe Cys Ser Pro Met Ile
            180                 185                 190

Thr Asn Pro Val Asp Phe Gly Val Asp Val Val His Ser Ala Thr
        195                 200                 205

Lys Tyr Ile Asn Gly His Thr Asp Val Val Ala Gly Leu Ile Cys Gly
```

```
            210                 215                 220
Lys Ala Asp Leu Leu Gln Gln Ile Arg Met Val Gly Ile Lys Asp Ile
225                 230                 235                 240

Thr Gly Ser Val Ile Ser Pro His Asp Ala Trp Leu Ile Thr Arg Gly
                245                 250                 255

Leu Ser Thr Leu Asn Ile Arg Met Lys Ala Glu Ser Glu Asn Ala Met
            260                 265                 270

Lys Val Ala Glu Tyr Leu Lys Ser His Pro Ala Val Glu Lys Val Tyr
        275                 280                 285

Tyr Pro Gly Phe Glu Asp His Glu Gly His Asp Ile Ala Lys Lys Gln
290                 295                 300

Met Arg Met Ser Gly Ser Met Ile Thr Phe Ile Leu Lys Ser Gly Phe
305                 310                 315                 320

Glu Gly Ala Lys Lys Leu Leu Asp Asn Leu Lys Leu Ile Thr Leu Ala
                325                 330                 335

Val Ser Leu Gly Gly Cys Glu Ser Leu Ile Gln His Pro Ala Ser Met
            340                 345                 350

Thr His Ala Val Val Pro Lys Glu Glu Arg Glu Ala Ala Gly Ile Thr
        355                 360                 365

Asp Gly Met Ile Arg Leu Ser Val Gly Ile Glu Asp Ala Asp Glu Leu
370                 375                 380

Ile Ala Asp Phe Lys Gln Gly Leu Asp Ala Leu Leu
385                 390                 395
```

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:13:

GGATTACATA TGCATCATCA TCATCATCAC ATGAGTGGCC ACGCTATCGA C        51

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

GGATTAGGAT CCTTAGAGGA CTAAGTCGAG AGCC        34

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:15:

ATCGCTAGCA TATGATCCCG GACGTATCAC AG        32

(2) INFORMATION FOR SEQ ID NO:16:

(i) SEQUENCE CHARACTERISTICS:
        (A) LENGTH: 22 base pairs

-continued (B) TYPE: nucleic acid
(C) STRANDEDNESS: single
(D) TOPOLOGY: linear (xi) SEQUENCE DESCRIPTION: SEQ ID NO:16:

ATCACCATCC ACTGGTGTAA TG                                                22

(2) INFORMATION FOR SEQ ID NO:17:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:17:

CTACCGATTT TGCGGAAG                                                     18

(2) INFORMATION FOR SEQ ID NO:18:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:18:

CATGACGGAT CCTCAGGCGT GTTTTTCCAG                                        30

(2) INFORMATION FOR SEQ ID NO:19:

(i) SEQUENCE CHARACTERISTICS:
    (A) LENGTH: 49 base pairs
    (B) TYPE: nucleic acid
    (C) STRANDEDNESS: single
    (D) TOPOLOGY: linear (xi) SEQUENCE DESCRIPTION: SEQ ID NO:19:

ATCGCTAGCA TATGCATCAT CATCATCATC ACATGATCCC GGACGTATC                   49

HIGH SPECIFICITY HOMOCYSTEINE ASSAYS FOR BIOLOGICAL SAMPLES

The present application is a continuation-in-part of U.S. application Ser. No. 09/122,129, filed Jul. 24, 1998, pending, which is itself a continuation-in-part of U.S. application Ser. No. 09/061,337, filed Apr. 17, 1998, pending, which is itself a continuation-in-part of U.S. application Ser. No. 08/974,609, filed Nov. 19, 1997, pending, which is itself a continuation-in-part of Ser. No. 08/941,921, filed on Oct. 1, 1997, abandoned, itself a continuation-in-part of U.S. application Ser. No. 08/918,214, filed on Aug. 25, 1997, abandoned, itself a continuation-in-part of U.S. application Ser. No. 08/899,776, filed on Jul. 24, 1997, abandoned, and each application incorporated by reference herein, in its entirely, as if fully set forth.

FIELD OF THE INVENTION

The present invention relates to the assay of homocysteine in biological fluids such as urine, whole blood, and blood plasma. More particularly, the invention relates to the use of enzyme preparations that comprise one or more homocysteinase enzymes and diagnostic kits containing these enzymes. In the preferred practice of the invention, homocysteine concentration is determined by measurement of hydrogen sulfide produced therefrom.

BACKGROUND ART

K. S. McCully et al. (*American Journal of Pathology*, 56, pp. 111–128, 1969) first reported the association of blood plasma homocysteine levels with risk from cardiovascular disease. McCully et al. identified a correlation between elevated plasma homocysteine concentrations and arteriosclerotic disease. More recent studies have determined that even moderately elevated plasma homocysteine levels are indicative of substantially increased risk to coronary heart disease, cerebrovascular disease, and peripheral vascular disorders. See, for example, J. Selhub et al., *New England Journal of Medicine*, 32, pp. 286–291, 1995, and S. Kang et al., *Annual Review of Nutrition*, 12, pp. 279–298, 1992.

With respect to assessing risk to cardiovascular disease, there is substantial evidence that elevated homocysteine levels may be a better predictor of risk than elevated cholesterol levels. For example, in one study, plasma homocysteine concentrations only 12% above the upper limit of normal were associated with a 3.4-fold increase in risk for myocardial infarction (M. Stampfer et al., *Journal of the American Medical Association*, 268, pp. 877–881, 1992). In another case study where blood was drawn before cardiovascular disease was diagnosed, a group of 271 men (who later suffered myocardial infarctions) presented significantly higher levels of homocysteine than control patients who did not later suffer infarctions (see P. Ueland et al., Cardiovascular Disease, Hemostasis and Endothelial Function, 1992, at pages 183–236, Marcel Dekker, New York).

O. Nygard et al., *New England Journal of Medicine*, 337(4), pp. 230–236 (1997) report that total plasma homocysteine is a strong predictor of mortality in patients with confirmed coronary artery disease.

A detailed understanding of the molecular mechanisms whereby homocysteine participates in cardiovascular disease processes has not yet been achieved. It has been suggested that homocysteine participates in reactions resulting, for example, in overproduction of oxygen free radicals, elastase activation, and calcium deposition (i.e. plaque formation). For a review of current theories, see K. McCully, *Nature Medicine*, 2(4), pp. 386–389 (1996) and K. S. McCully, *Annals of Clinical and Laboratory Science*, 23(6), pp. 477–493 (1993). Elevated levels of circulating homocysteine may also affect the coagulation process directly (see O. Nygard et al., above, and references cited therein).

Accordingly, there is a need to develop accurate methods to determine homocysteine levels in patients, and to make such assays a recognized part of standard medical practice. As described below, there is also a critical need to make available widespread screening of infants for diseases involving abnormal homocysteine metabolism, such as homocystinuria.

REPORTED DEVELOPMENTS

A. Araki et al., *Journal of Chromatography*, 422, pp. 43–52 (1987) describe a detection method for free and protein bound homocysteine in plasma that utilizes reaction with a thiol specific fluorogenic agent, followed by detection with high pressure liquid chromotogaphy (HPLC) to separate other thiol species. See also N. P. B. Dudman et al., *Clinical Chemistry*, 42(12), pp. 2028–2032 (1996). Disadvantages of such methods for clinical application may include the inherent limits on the number of samples that can be processed by HPLC, that use of HPLC may not permit high through-put screening, and that appropriate HPLC machines may not be present in clinical labs.

Shipchandler et al. (see *Clinical Chemistry*, 41(7), pp. 991–994, 1995) have recently described a fluorescence polarization immunoassay for detection of homocysteine, and of homocystine (the disulfide dimer of homocysteine). The assay was stated to evidence little cross reactivity toward cysteine and methionine. The assay involves conversion of homocysteine to S-adenosylhomocysteine, and detection is based on use of a monoclonal antibody that recognizes S-adenosylhomocysteine, and also a fluorescein analog thereof. However, potential disadvantages of this detection technology may include cost associated with monoclonal antibody production and "nonspecificity" of the antibody, that is, cross reactivity toward, for example, S-adenosyl methionine. Additionally, it appears that this method can only be practiced with particular patented instrumentation available from only once source.

K-W. Thong et al. (*Experimental Parasitology*, 63, pp. 143–151, 1987) describe enzymatic conversion of homocysteine to alpha-ketobutyrate, hydogen sulfide and ammonia followed by determination of the hydrogen sulfide with lead acetate (see also K-W. Thong et al., *IRCS Medical Science*, 13, pp. 493–494, and pp. 495–496, 1985) However, there is no suggestion of use of the involved enzyme (for example, from the parasite *Trichomonas vaginalis*) for clinical diagnosis. Additionally, in a clinical context, the disclosed procedure does not distinguish homocysteine from cysteine, nor does it account for that fraction of homocysteine molecules in biological samples that is disulfide bonded, or bonded to protein.

An additional procedure for detection of homocysteine that involves use of a microbial enzyme from the bacterium *Pseudomonas ovalis* is disclosed in Yamaguchi et al., *Annual Report of Sapporo City Institute of Public Health*, No. 20, pp. 67–74, 1993. The authors focused on detection of the amino acid methionine as an indirect method to determine homocysteine levels (such as for homocystinuria patients), since homocysteine was considered unstable, for example being prone to disulfide bonding with proteins.

As an indirect measure of homocysteine, it is possible that the method is less accurate, and determination of product ammonia instead of product hydrogen sulfide may be less sensitive given the high background levels of ammonia in biological fluids. It is noted also that ammonia assays are adversely affected by the presence of contaminating deaminases, a potentially pervasive problem. Similarly, assay of product alpha-keto butyrate is expected to be ineffective given the high background level in biological samples (for an assay procedure, see Y. Tan et al., *Protein Expression and Purification,* 9, pp. 233–245, 1997).

An additional reference of relevance to the practice of the invention is U.S. Pat. No. 5,631,127 to Sundrehagen, issued May 20, 1997.

Given the increasing awareness of the role of homocysteine in cardiovascular disease, and the public health goal to screen patients for risk from cardiovascular disease, there is a critical need for novel analytical procedures that can be used to accurately determine homocysteine levels in patients. Such procedures are expected to provide considerable medical benefit both in those cases where elevated homocysteine concentrations are a cause of a particular disease state, and in cases where elevated homocysteine concentrations are a detectable byproduct of an exisiting disease state.

Such analytical procedures would also provide great benefit by predicting a patient's susceptibility to cardiovascular disease before onset can be detected by other procedures. In this regard, great benefit would be achieved by adapting such procedures to the widespread screening of the general population, and in particular, to all infants. The present invention provides for such methods, including diagnostic kits for use in the clinical setting.

In connection with the design of such improved analytical procedures, it would be of great value to develop enzymes useful to measure homocysteine in single step/enzyme assay, but which are substantially non-reactive toward the interfering concentrations of cysteine and methionine that are typically present in biological samples. As described below, the present invention provides for homocysteinase enzymes which have such specificity.

SUMMARY OF THE INVENTION

The present invention provides for novel methods to determine the concentration of homocysteine in biological fluids. In a preferred embodiment of the invention, the biological fluid is a urine, tissue fluid, blood, blood serum, or blood plasma sample from a patient, and the methods of the invention are useful to assess risk for cardiovascular disease. In particular, the present invention provides novel methods to determine homocysteine concentrations in biological fluids while avoiding detection of related but interferring substances, most particularly cysteine and methionine.

Accordingly, there is provided a method for determining the amount of homocysteine that is present in a biological sample containing, for example, homocysteine and cysteine, that comprises contacting said sample with an enzyme preparation capable of producing hydrogen sulfide from homocysteine and cysteine, and determining the amount of homocysteine in said sample by measuring the amount of hydrogen sulfide produced from homocysteine. In a most preferred embodiment, the enzyme preparation consists only of a single enzyme whose reactivity toward homocysteine is sufficient, compared to cysteine, that hydrogen sulfide produced from cysteine may be ignored.

Said enzyme preparation comprises an enzyme referred to as a homocysteinase, and which may be referred to by other names as described below. Additionally, the term "enzyme preparation" should also be understood to include, unless otherwise noted, both a single and a plurality of aliquots, that is, either a single amount or multiple amounts of one or more enzymes may be added during the course of an assay procedure, and the use of the term is without limitation has to how, or how many, aliquots or steps are used to add all of the necessary enzymes during a reaction procedure.

According to a preferred aspect of the invention, it is recognized that the total concentration of homocysteine present in biological samples, for example in body fluids, includes homocysteine molecules that are not present in free form, being instead covalently coupled to other molecules. The methods of the invention provide further steps for releasing this homocysteine prior to measuring of homocysteine-derived hydrogen sulfide.

It should be noted, however, that since the methodology of the present invention provides for accurate measurement of free homocysteine levels absent interference from related substances (for example, cysteine), valuable information is provided to the clinician even if only free homocysteine is detected. Among many uses, it is expected that such information is very useful as a fast initial diagnostic tool, for example, in the testing of all newborn infants.

Additional embodiments of the invention include methods to distinguish homocysteine from any cysteine that may be present in said biological sample. Representative of such methods are:

(I) a procedure wherein hydrogen sulfide produced from homocysteine is distinguished from hydrogen sulfide produced from cysteine by including in said method the additional initial steps of:
 (a) contacting said biological sample with a reagent that protects homocysteine from said enzyme preparation;
 (b) permitting said enzyme preparation to produce hydrogen sulfide from cysteine present in said sample;
 (c) removing said hydrogen sulfide; and
 (d) deprotecting said homocysteine, and adding a further amount of enzyme preparation to produce hydrogen sulfide therefrom; and (II) a procedure that includes the additional initial steps of:
 (a) contacting homocysteine that is present in said biological sample with a further enzyme preparation capable of converting it to a compound that can be isolated;
 (b) isolating said compound;
 (c) contacting said compound with an enzyme preparation or other reagent under conditions where said compound is converted back to homocysteine; and
 (d) contacting the homocysteine so produced with said enzyme preparation capable of producing hydrogen sulfide therefrom;

(III) a procedure wherein said biological sample is pre-treated with an agent that renders cysteine non-reactive to said enzyme preparation; and (IV) a procedure wherein hydrogen sulfide produced from homocysteine is distinguished from hydrogen sulfide produced from cysteine, that includes the steps of:
 (a) permitting an enzyme preparation to produce hydrogen sulfide from both homocysteine and cysteine present in said sample, wherein said enzyme also produces pyruvate from cysteine in an amount equal to the amount of hydrogen sulfide produced therefrom;
(b) determine the amount of pyruvate so produced; and
(c) calculate the amount of homocysteine from the amount of hydrogen sulfide attributed thereto, wherein said sample is, or optionally is not, divided into a first part and a second part in order to conduct said assays.

In a particularly preferred embodiment of the invention that is readily adapted to the rapid testing of samples from a large number of patient samples, there is provided a method for determining the amount of homocysteine that is present in a biological sample containing homocysteine and cysteine, comprising the steps of:
(a) dividing said sample into 2 parts, part 1 and part 2;
(b) contacting part 1 with a first enzyme preparation that is capable of converting homocysteine to a substance that is not a substrate for homocysteinase, wherein said first enzyme preparation does not recognize cysteine as a substrate;
(c) independently contacting part 1 and part 2 with a second enzyme preparation that comprises a homocysteinase capable of producing hydrogen sulfide from both homocysteine and cysteine;
(d) measuring the amount of hydrogen sulfide produced in part 1 and part 2; and
(e) calculating the amount of homocysteine in said biological sample by subtracting the hydrogen sulfide measurement of part 1 from that of part 2, and doubling the result.

For the clinical practice of the invention, there is provided a diagnostic kit for use in determining the amount of homocysteine in a biological sample, and wherein the homocysteinase included therewith is obtained from one of several sources. In a preferred embodiment, the diagnostic kit comprises:
(a) a homocysteinase from *Trichomonas vaginalis*, or *Pseudomonas* (such as species *ovalis* or *putida*), and
(b) at least one reagent capable of being used to determine the amount of hydrogen sulfide formed in the homocysteinase reaction.

In a further aspect of the invention, there is provided a chimeric nucleotide sequence (whether of DNA or RNA), derived from more than one gene, or other polynucleotide, that codes for a homocysteinase, wherein expression of such sequence leads to the production of a chimeric homocysteinase. Such homocysteinases have valuable properties with respect to the practice of the invention, and a preferred example thereof includes a chimeric enzyme that comprises amino acid sequences derived from both *Trichomonas vaginalis* and *Pseudomonas putida* homocysteinases.

Thus the present invention provides two basic approaches in the design of clinical assays for homocysteine: (1) to enhance detection of homocysteine in biological samples using novel assay techniques to detect homocysteinase reaction products, and (2) to further enhance the sensitivity of such assays by designing homocysteinase enyzmes that have substantially enhanced reactivity toward homocysteine, in comparison with other sulfur-containing amino acids.

With respect to approach (2) above, use of the protein encoded by SEQ ID NO:10 is representative. Such a homocysteinase enzyme is sufficiently non-reactive toward cysteine or methionine that the concentration of homocysteine that is present, for example, in a sample of tissue fluid, urine, blood, blood serum, or blood plasma of a subject may be determined in a single step assay, wherein is measured the amount of one or more products resulting from reaction of said homocysteinease on homocysteine in said sample, and wherein said measurement is substantially unaffected by the concentration of cysteine or methionine therein.

In a preferred aspect, such a homocysteinase is patterned on a homocysteinase from Pseudomonas, Clostridium, Aeromonas or Trichomonas, and in an example thereof, one or more peptide sequences of such an enzyme are correspondingly replaced by one or more homologous peptide sequences of SEQ ID NO: 10, for example, those selected from the group consisting of:
(a) Gly-Gly-Asn-Arg-Leu-Ala-Gly-Gln-Glu, (see residues 43–51 of SEQ ID NO:10);
(b) a subset of (a) that comprises Leu;
(c) Arg-Val-Cys-Lys-Glu-Ala-His-Ser-Gln, (see residues 168–176 of SEQ ID NO:10);
(d) a subset of (c) that comprises Glu;
(e) Gln-Met-Arg-Met-Tyr-Gly-Ser-Met-Ile, (see residues 304–312 of SEQ ID NO: 10); and
(f) a subset of (e) that comprises Tyr.

In a preferred aspect, such a homocysteinase is a substitution variant, addition variant, deletion variant, or derivative of SEQ ID NO:10, wherein said variant or derivative has one or both of the following properties:
(a) at least about 10% of the activity of SEQ ID NO:10 toward homocysteine in a suitable assay; and/or
b) no more than about 1000% of the activity of SEQ ID NO:10 toward cysteine (or ethionine) in a suitable assay.

Additional aspects of the invention therefore include: (1) a purified and isolated DNA molecule that comprises a nucleotide sequence coding for a homocysteinase having such specificity, and wherein said coding sequence is operably linked to control sequences capable of directing expression therefrom in a host cell; and (2) appropriately transfected host cells.

An additional preferred embodiment of the invention is a method for determining the amount of homocysteine that is present in a biological sample containing homocysteine and cysteine, which method comprises measuring the concentration of a product that is produced from homocysteine in a reaction catalyzed by a homocysteinase, which product may also be produced by reaction of said homocysteinase upon cysteine in said sample, and wherein said sample contains an otherwise interfering concentration of cysteine, said method comprising the steps of:
(a) incubating said sample with γ-glutamylcysteine synthetase in the presence of substrates that permit conversion of cysteine to γ-glutamylcysteine;
(b) incubating the mixture resultant from step (a) with homocysteinase; and
(c) measuring the concentration of a product that is capable of being produced from both homocysteine and cysteine in a reaction catalyzed by a homocysteinase, and wherein it is preferred (1) to use as homocysteinase the *Trichomonas vaginalis* enzyme corresponding to SEQ ID NO:10, or to residues Met$^1$ through Leu$^{396}$ thereof, and (2) to use *E. coli* γ-glutamylcysteine synthetase. Diagnostic kits are also provided, as is an analogous procedure based upon the use of cysteine tRNA synthetase.

Additional important features of the invention include a diagnostic kit for use in a single enzyme assay of the homocysteine concentration in a biological fluid of a subject, said kit comprising:
(a) a homocysteinase enzyme; and
(b) at least one reagent capable of being used to determine the amount of product hydrogen sulfide formed by reaction of homocysteinase on homocysteine; wherein said homocysteinase is sufficiently non-reactive toward cysteine that any hydrogen sulfide produced by reaction of said homocysteinase on cysteine does not substantially interfere with the use of said kit to assess risk for cardiovascular disease.

According to this aspect of the invention, a diagnostic kit is typically provided wherein the homocysteinease included therein has the property that at least about 90% of the hydrogen sulfide produced by action of said homocysteinase upon contacting a biological sample in an assay for homocysteine is contributed by said homocysteine when, for example, the concentrations of homocysteine and cysteine in said fluid are, respectively, about 20 μmolar and about 300 μmolar respectively. Preferably, the included homocysteinase has the property that at least about 99% of the hydrogen sulfide produced by action of said homocysteinase upon contacting said biological fluid is contributed from homocysteine. Such diagnostic kits can be used, for example, to accurately determine the homocysteine concentration in biological fluids in the range of about 1–500 μmolar, or higher as necessary, wherein said fluids also contains from 0 to about 1000 μmolar of cysteine, in a typical example.

With respect to the use of such kits, as with other assay procedures of the invention, it is generally preferred to include use of a disulfide reducing agent, such as dithiothreitol ("DTT"), so that homocysteine molecules in biological samples that are disulfide-bonded to other molecules (such as free cysteine, other homocysteine molecules or protein SH groups) can also be detected.

A preferred embodiment of this invention is a diagnostic kit comprising:

(a) SEQ ID NO: 10, or residues $Met^1$ through $Leu^{396}$ thereof, as homocysteinase in a concentration of 0.01–1000 μM/ml;

(b) at least one buffer having a concentration of 10 mM–1 M and a pH of 7–9.5 selected from the group consisting of sodium phosphate buffer, tris buffer and borate buffer; and at least one reducing agent having a concentration of 0.1 mM–1 M elected from the group consisting of DL-dithiothreitol, TCEP, and β-mercaptoethanol; 0.01–100 mM potassium ferricyanate, 0.1–10% w/v surfactant (detergent); a 0.01–100 mM solution of N,N-dialkyl-phenylene diamine having a dialkyl group selected from the group consisting of dimethyl, diethyl, dipropyl and dibutyl; and (c) homocysteine and/or homocystine as a calibration standard.

It is preferred that in such method homocysteinase is added to a sample in an amount needed to achieve a final concentration of 0.01–1000 μg/ml; and reagents are added in amounts needed to achieve final concentrations of 1–100 mM of buffer, even more preferably 5–50 mM; 0.01–100 mM reducing agent, even more preferably 0.1–10 mM; 0.01–10 mM potassium ferricyanate, even more preferably 0.05–5 mM, 0.01–1.0% w/v surfactant, even more preferably 0.05–0.5%; and about 0.01–10 mM solution of N,N-dialkyl-phenylene diamine, even more preferably 0.1–10 mM.

Further representative and additional aspects of the invention are described according to the Detailed Description of the Invention which follows directly. It should be recognized also that the practice of the present invention should not be seen as dependent on, or limited by, any particular theory concerning the role of homocysteine in pathological processes.

BRIEF DESCRIPTION OF THE DRAWINGS

FIG. 1 (panels A and B) provides a comparison of the amino acid sequence of Trichomonas vaginalis homocysteinase encoded by the mgl1 gene with that encoded by the Trichomonas vaginalis pAC2-1 clone.

DETAILED DESCRIPTION OF THE INVENTION

Figure 2:
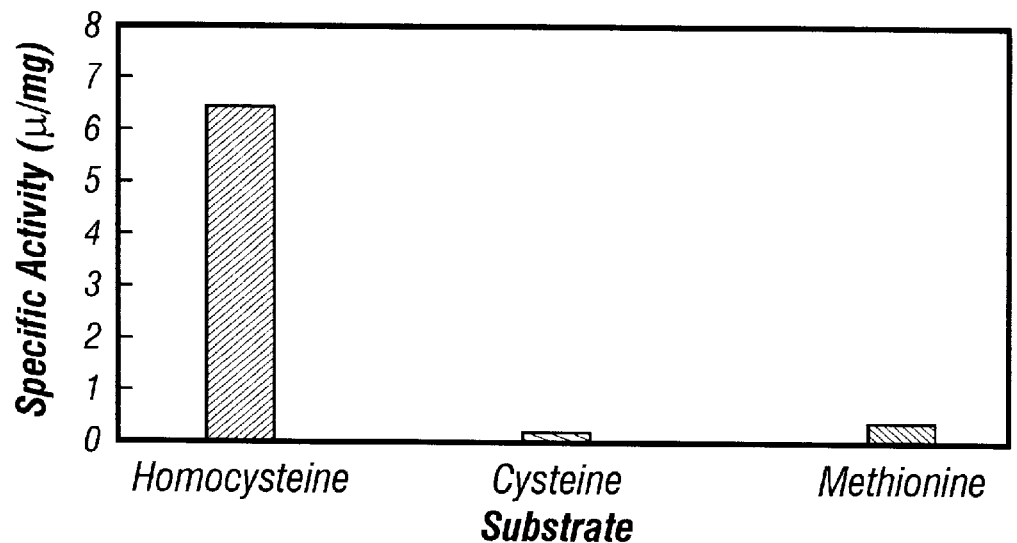
FIG. 2 shows the comparative specific activities (units/mg crude E. coli extract) corresponding to homocysteinase of the pAC2-1 clone for cysteine, methionine, and homocysteine.

Elevated blood plasma homocysteine levels are recognized as a risk factor for vascular disease. The atherogenic properties of homocysteine were first noted in association with a rare group of genetic diseases referred to collectively as homocystinuria. The disease state is characterized by a level of circulating homocysteine that is typically 10-fold (or greater) above that in normal blood. Under these circumstances, homocysteine is also detected in the urine. Premature vascular disease is strongly correlated with this condition. For example, if homocystinuria is left untreated, about 50% of patients suffer thromboembolic events, and mortality by the age of 30 is approximately 20% (see, for example, S. H. Mudd et al., American Journal of Human Genetics, 37, pp. 1–31, 1985).

Given that more than 75 epidemiologic or clinical studies have now shown a relation between total homocysteine levels and coronary and peripheral arterial diseases, stroke, and venous thrombosis, there is a clear medical need for diagnostic procedures that can accurately determine homocysteine levels in, for example, blood plasma. It would be highly advantageous also if such methods could be adapted to mass screenings of large populations of patients, or of the general population or newborn infants. The development of such assay procedures has been hindered principally by two interrelated difficulties:

(1) the chemical and biochemical properties of homocysteine are intimately related to those of other sulfhydryl-containing biomolecules, including the amino acids methionine and cysteine, and thus improved assay procedures for homocysteine must be uniquely responsive to homocysteine.

(2) homocysteine is highly reactive and exists under physiological conditions in many forms besides the free homocysteine molecule, for example, as a disulfide-linked dimer, as a disulfide-linked heterodimer with free cysteine, as a disulfide-linked conjugate with cysteine residues of blood plasma proteins, and bonded (often as an N-Acyl derivative) to the R groups of other protein amino acids (for example, to the epsilon amino group of protein lysine). These conjugated forms contribute very substantially to the total amount of homocysteine that may participate in pathological processes. Given also that only minor increases, beyond the normal range, in plasma homocysteine concentrations lead to satistically significant disease risk (see, O. Nygard et al. above), it is useful that clinical assays provide the capability to detect the total homocysteine content of biological fluids. This said, the reproducible detection of free homocysteine (or of any of the other forms in which homocysteine is found), but absent interference from such other substances as methionine and cysteine, also provides valuable information to the clinician.

The present invention is thus directed to the development of homocysteine assay procedures, and the selection of reagents therefor, that overcome the above complexities under conditions where large scale screening of patient samples is practicable.

Homocysteinase Enzymes Useful in the Practice of the Invention

According to the practice of the invention, homocysteine concentrations in biological samples are determined enzymatically with enzymes hereinafter referrred to as "homocysteinases", which are defined as enzymes capable of catalyzing reactions whereby hydrogen sulfide is produced from homocysteine. In the typical case, ammonia and alpha-ketobutyrate are also produced. As described herein, it is preferred to detect product hydrogen sulfide, although product ammonia and/or alpha-ketobutyrate or other products may also be detected. Homocysteinases, as defined herein, may catalzye other reactions involving other sulfhydryl compounds and have acquired multiple names in the literature; however, they are generally useful in the practice of the present invention if they possess the property of catalyzing production of hydrogen sulfide from homocysteine.

A first homocysteinase that is preferred in the practice of the invention is L-methionine-alpha-deamino-gamma-mercaptomethane lyase (methionine lyase) derived from the bacterial source, *Pseudomonas putida*. The enzyme has been purified by S. Ito et al., *Journal of Biochemistry*, 79, pp.1263–1272 (1976), and determined to have a molecular weight of about 170 kDa. In the context studied by S. Ito, the enzyme carried out the alpha-gamma elimination of methionine to alpha-keto butyrate, methanethiol, and ammonia. If homocysteine is the substrate, then alpha-keto butyrate, hydrogen sulfide, and ammonia would be the resultant products. The homologous enzyme has been isolated from *Pseudomonas ovalis*, H. Tanaka et al., Biochemistry, 16, pp.100–106 (1977). Methods for the recombinant production of this Pseudomonas enzyme have also been developed (see Y. Tan et al., *Protein Expression and Purification*, 9, pp. 233–245, 1997), and use of recombinant enzyme in the clinical practice of the present invention is expected to provide advantages in terms of diagnostic kit cost and assay reproducibility. The Tan et al. reference describes construction of a clone designated pAC1-1 containing a single copy of enzyme-encoding sequence. An additional clone, designated pAC1-11, has been constructed which contains two copies of the encoding sequence, in tandem. As with the pAC1-1 structure, the pT7-7 plasmid was used to construct pAC1-11. The two encoding sequences are linked together at a BamHI site, with the first gene linked NdeI to BamHI, and the second linked BamHI to a further BamHI site.

The substrate specificity of the *P. putida* enzyme has also been determined. For example, N. Esaki et al. *Methods in Enzymology*, 143, pp. 459–465 (1987) report that on a relative activity scale where activity toward methionine is assigned 100, cysteine is 10, and homocysteine is 180. That the enzyme is reactive to all three sulfhydryl-containing amino acids underscores the need to define clinical assays for which the source of hydrogen sulfide can be properly determined. It should be noted that the apparent 10-fold preference of the enzyme for homocysteine over cysteine does not take into account that the concentration of cysteine in a biological sample may be high—in fact much higher than the concentration of homocysteine. Homocysteinase enzymes of suitable catalytic activity can be derived from other Pseudomonas species, or from other bacteria, using routine screening procedures and assays that are recognized in the art.

An additional group of organisms that are a source of homocysteinase useful in the practice of the invention are species of the Trichomonad parasites and related protozoans. Trichomonads are important parasites of the urogenital tract and are aerotolerant (but nonetheless anaerobic) flagellate protozoa. Use of homocysteinase from *Trichomonas vaginalis* is preferred according to the practice of the invention.

Trichomonas species are believed to use their capabilities for thiol metabolism in order to counter oxygen toxicity in host tissues, see K-W Thong et al., *Experimental Parasitology*, 63, pp.143–151 (1987), and papers cited therein. Although considerable variation in homocysteinase activity (termed homocysteine desulphurase activity therein) was found between Trichomonas species, it is routine to screen available species for acceptable levels of enzyme activity. Generally speaking, it is preferred that a homocysteinase should have a specific activity of at least about 1 unit/mg purified protein for use in the below-described assays, although it is well within the skill of those familiar with the relevant art to design variations on these assays that use greater or lesser amounts of enzyme or enzyme preparations with differing enzyme activity. It is noted that highly purified and active *P. putida* enzyme has a specific activity of about 20 units/mg (a unit of enzyme activity may be described as 1 micromole of substrate converted per minute under standard conditions (see Y. Tan et al. above).

The "homocysteine desulphurase activity" reported by K-W. Thong et al. (1987) above appears to result from the same enzyme responsible for methionine catabolizing activity in Trichomonas, and later termed methionine-gamma-lyase by B. C. Lockwood and G. H. Coombs (*Biochemical Journal*, 279, pp. 675–682, 1991) wherein is also described purification of this enzyme. As aforementioned, use of methionine-gamma-lyase (a homocysteinase) from *Trichomonas vaginalis* is preferred in the practice of the present invention.

Use of a recombinant version of the *T. vaginalis* enzyme is also preferred. One potential cloning strategy follows the observations by A. Marcos et al., FEMS Microbiology Letters, 135, pp. 259–264 (1996), that *T. vaginalis* genes may have few introns. Accordingly, a genomic library would be constructed (see D. E. Riley et al. *Molecular and Biochemical Parasitology*, 51, pp. 161–164, 1992) and screened with DNA fragments corresponding to the *Psuedomonas putida* enzyme, and which are expected to reflect some partially conserved sequence.

Lockwood et al. also list other reports of bacteria having methionine-gamma-lyase activity involving species of Pseudomonas, Clostridium, and Aeromonas.

It is expected that such species are sources of homocysteinase activity useful in the practice of the present invention. Additional organisms that are expected to provide useful homocysteinase enzymes are certain marine algae (see, for example, D. A. Gage et al. *Nature,* 387, pp. 891–897, (1997) describing species with extensive methionine-related metabolism); sulfur bacteria; and geomicrobes or other microbes living under extreme environmental conditions (see, for example, R. A. Kerr, *Science,* 276, pp.703–704, 1997 and E. Pennist, *Science,* 276, pp.705–706, 1997). Additional examples of microorganisms that may be useful sources for homocysteinase-type enzymes include bacteria involved in periodontal disease, such as are capable of forming volatile sulfur compounds from cysteine. In this regard, see S. Persson et al., *Oral Microbiology and Immunology,* 5(4), pp. 195–201, 1990.

Finally, with respect to the definition of "homocysteinases" that are useful in the practice of the invention, it should not be viewed as a limitation herein that hydrogen sulfide necessarily be a product of such enzymes. Broadly speaking, the present invention provides for high through-put diagnostic procedures, permitting the cost effective analysis of a very large number of homocysteine-containing samples while avoiding detection of interfering substances.

Accordingly, it is expected that other enzymes that metabolize homocysteine are useful in the practice of the invention if methods exists to detect such metabolites under conditions where interference from substances similar to homocysteine (such as cysteine) can be avoided. The following examples describe a considerable spectrum of techniques to accurately measure homocysteine while avoiding detection of interfering substances. Accordingly, it will be appreciated that the techniques disclosed below can be adapted by those skilled in the art to detection methods using many other enzymes that act on homocysteine.

Chimeric Homocysteinases

As aforementioned, in a preferred aspect of the invention there is provided a chimeric nucleotide sequence (whether of DNA or RNA), derived from more than one gene (or other polynucleotide such as a cDNA or other intron-less sequence), that codes for a chimeric homocysteinase enzyme.

Such homocysteinases have properties that are very useful with respect to the practice of the invention, and a preferred example thereof includes a chimeric enzyme that comprises amino acid sequences corresponding to both *Trichomonas vaginalis* and *Pseudomonas putida* homocysteinases.

It is believed that *P. putida* homocysteinase is more stable than the *T. vaginalis* enzyme under a variety of conditions. As one probable consequence thereof (see B. Lockwood et al., *Biochemical Journal,* 279, pp. 675–682, (1991), recovery of the *T. vaginalis* enzyme during purification was very low (see p. 679 at Table 2, referring to "methionine γ lyase"). Thus in the practice of the present invention, it is preferred to include *P. putida* sequences in chimeric enzymes in order to take advantage of this enhanced stability.

As discussed above, different homocysteinases have different respective reactivities toward their various sulfur-containing substrates, for example, cysteine, methionine, and homocysteine. Although the selection of particular reaction conditions may affect apparent reactivities under particular circumstances, evidence indicates that the *T. vaginalis* enzyme has a higher reactivity toward homocysteine as substrate than does the *P. putida* enzyme, which may show greater reactivity toward cysteine, or methionine as substrate. In this regard, the results reported by Lockwood et al., 1991 at Table 4 thereof) are of note in that relative activity data for the *T. vaginalis* enzyme evidence a very pronounced "preference" for homocysteine as substrate (see also the $K_m$ data reported on page 678 thereof). This is in contrast to the data reported by N. Esaki et al. above with respect to the *P. putida* enzyme.

Thus, the properties of homocysteinease for use in the clinical diagnostic applications of the present invention can be improved by providing the enzyme as a chimeric molecule that draws upon functional features contributed to the chimeric protein from both of its component species. In particular, it is preferred to select for inclusion in the chimeric homocysteinases of the invention regions of the *P. putida* enzyme that contribute substantially to the stability thereof, while including also regions of the *T. vaginalis* enzyme that preferentially enhance reactivity toward homocysteine as substrate.

In connection with the design of such enzymes, a recent report that *T. vaginalis* homocysteinase actually represents two protein species derived from two genes is of note (see J. C. Mottram, direct submission of sequences to Gene Bank, submitted Jul. 17, 1997, as *T. vaginalis* mgl1 gene, accession number AJ000486, NID g2330884, and *T. vaginalis* mgl2 gene, accession number AJ000487, NID g2330886), the complete sequences of which are fully incorporated by reference herein, as if directly set forth. See also International Patent application WO 98/07872 published Feb. 26, 1998, and A. McKie et al., *Journal of Biological Chemisty,* 278, pp.5549–5556, 1998.

The present invention therefore provides for a purified and isolated DNA molecule comprising a chimeric nucleotide sequence that encodes amino acid sequence of *Pseudomonas putida* homocysteinase, and amino acid sequence of *Trichomonas vaginalis* homocysteinase (derived from either mgl1, or mgl2, or both) from which can be expressed a functional protein having homocysteinase activity. In a preferred aspect, the nucleotide construct (or corresponding amino acid construct) corresponds predominantly to that of *P. putida,* and thus there is provided a DNA molecule that comprises an encoding nucleotide sequence for *Pseudomonas putida* homocysteinase, wherein one or more subsequences thereof that encode one or more amino acids of said enzyme are correspondingly replaced by one or more nucleotide subsequences that encode the corresponding amino acids of a *Trichomonas vaginalis* homocysteinase. In the practice of the present invention, the *T. vaginalis* enzyme encoded by the mgl1 gene is hereinafter referred to as the T1 protein, and that encoded by the mgl2 gene is referred to as the T2 protein.

In connection with the selection of chimeric polypeptides and encoding polynucleotides, the following considerations are of note. The T1 and T2 proteins are encoded by remarkably similar DNA sequences. Accordingly, it is generally expected to be the case that substitution of an mgl1-encoding subsequence into a *P. putida* backbone will have substantially the same effect, and generate improvements substantially similar to those resultant from an equivalent mgl2 subsequence substitution.

However, it is noted that there are a limited number of subregions where the T1 and T2 sequences differ substantially, while at the same time, the T1 sequence (less so the T2 sequence) shows substantial homology with the published *P. putida* sequence. Indeed, the published *P. putida* sequence shows considerable homology with the T1 sequence.

Thus, in a further preferred aspect of the invention, there are identified regions of the encoding sequence for *T. vaginalis* enzyme where the T2 sequence and corresponding T1 sequence are very different from each other, and yet the T1 sequence is substantially similar to that of *P. putida*. Without being limited as to theory, it is believed that these encoding subregions of T2 present unique opportunities to insert into the a *P. putida* encoding polynucleotide, amino acid sequence domains that provide enhanced reactivity of the chimeric species toward homocysteine, thereby facilitating the diagnostic procedures of the invention.

The invention therefore provides for a DNA molecule that comprises an encoding sequence for *Pseudomonas putida* homocysteinase, wherein one or more subsequences thereof, that each encode one or more amino acids of said enzyme, are correspondingly replaced by one or more nucleotide subsequences than each encode the one or more corresponding amino acids of a *Trichomonas vaginalis* homocysteinase, and wherein said resultant amino acid replacements are selected from the group consisting of:

(a) Cys-Ser-Arg-Ala-Asp-Ile-Ile-Ala-Lys-Val-Lys-Ser (SEQ ID NO: 1), or any subset thereof, from *Trichomonas vaginalis* (T2) for Val-Gly-Ser-Gln-Ala-Leu-Val-Asp-Arg-Ile-Arg-Leu (SEQ ID NO: 2), or any subset thereof, from *Pseudomonas putida;*

(b) Asp-Val-Asp (SEQ ID NO: 3), or any subset thereof, from *Trichomonas vaginalis* (T2) for Glu-Leu-Lys (SEQ ID NO: 4), or any subset thereof, from *Pseudomonas putida;*

(c) Cys-His-Val-Val (SEQ ID NO: 5), or any subset thereof, from *Trichomonas vaginalis* (T2) for Ala-Leu-Gln-Leu (SEQ ID NO: 6), or any subset thereof, from *Pseudomonas putida;*

(d) Cys-Glu-Asn-Val-Gln-Asp-Ile-Ile-Asp-Asp (SEQ ID NO: 7), or any subset thereof, from *Trichomonas vaginalis* (T2) for Gly-Leu-Glu-Asp-Ile-Asp-Asp-Leu-Leu-Ala (SEQ ID NO: 8), or any subset thereof, from *Pseudomonas putida;* and (e) any combination involving one, two, three or four of the replacements provided for by groups (a), (b), (c), and (d) above.

With respect to the above-listed *Trichomonas vaginalis* mgl2 ("T2") amino acid subsequences it should be noted they correspond approximately to the following amino acid sequence positions:

Cys-Ser-Arg-Ala-Asp-Ile-Ile-Ala-Lys-Val-Lys-Ser (SEQ ID NO:1), approximately 226–237;
Asp-Val-Asp (SEQ ID NO:3), approximately 318–320;
Cys-His-Val-Val (SEQ ID NO:5), approximately 331–335; and
Cys-Glu-Asn-Val-Gln-Asp-Ile-Ile-Asp-Asp (SEQ ID NO:7), approximately 381–390.

In connection with the practice of this aspect of the invention, the above-listed *T. vaginalis* subsequences can be additionally modified to accept conservative amino acid substitutions. Additionally, the *T. vaginalis* subsequences need not correspondingly replace the above listed *P. putida* sequences so that, for example, the *T. vaginalis* subsequences may be inserted nearby (i.e. up to about 10 amino acid positions distant therefrom), while the targeted *P. putida* sequences remaining in place, in whole or in part. Additionally, the *T. vaginalis* inserts may comprise transfer of additional amino acids found on the N-terminal or C-terminal side of the above-depicted sequences thereof, as long as the benefit of increased reactivity toward homocysteine is not compromised owing to decreased enzyme stability.

The construction of appropriate chimeric encoding polynucleotides is straightforward for those familiar with the art, and may involve techniques of site directed or loop out mutagenesis, or use of PCR technology. Appropriate host cells for the expression of such encoding polynucleotides are described, for example, in Y. Tan et al., *Protein Expression and Purification*, 9, pp. 233–245, 1997.

Homocysteinases for One Step Assays that Lack Reactivity Toward Cysteine

According to the practice of the invention, there are also provided novel homocysteinase enzymes that are essentially non-reactive toward cysteine, that is, any such reactivity is sufficiently low that the amount of homocysteine present in a sample of tissue fluid, urine, blood, blood serum, or blood plasma, or other biological fluids or samples from human subjects, may be determined in a single enzyme assay—absent the need to correct for the concentrations of cysteine and/or of methionine that are also present in the sample. The significance of these discoveries will be immediately apparent to the clinician, given the widespread public health need for simple and fast homocysteine assays, when it is recognized that the concentration of cysteine and/or of methionine in such biological samples is generally much higher than that of homocysteine, and particularly so in certain disease states. Although such enzymes may react with methionine, this is generally irrelevant since a different detectable reaction product (hydrogen sulfide) results.

In this regard, the activity of the novel *Trichomonas vaginalis* homocysteinase represented by SEQ ID NO: 10 is of particular note (see Example 8, and FIGS. 2 through 4, as discussed further below). The relative activity of this enzyme toward homocysteine, compared to cysteine, will readily permit homocysteine measurements without the need to correct for any cysteine present in the biological test sample.

In a preferred example of the invention, such novel enzymes are patterned on homocysteinases found in various microorganisms including Pseudomonas, Clostridium, Aeromonas or Trichomonas, and particularly preferred homocysteinases are derived from *T. vaginalis*, including that expressed from the mgl1 gene (SEQ ID NO:11), or the mgl2 gene thereof.

In FIG. 1 (panels A and B) are depicted the amino acid sequences of two *Trichomonas vaginalis* homocysteinases, the first derived from a novel clone (pAC2-1) of the present invention, and the second, the enzyme derived from the known mgl1 gene (see also SEQ ID NOS:10 and 12 for comparison of amino acids; SEQ ID NOS: 9 and 11 for comparison of encoding DNAs). It will be seen that pAC2-1 is characterized by the existence of three differences (mutations), compared to mgl1:
Phe to Leu at amino acid position 47,
Asp to Glu at amino acid position 172, and
Ser to Tyr at amino acid position 308.

Modified homocysteinase amino acid sequences, made by incorporating amino acid substitutions that include one or more of these differences (mutations), are particularly useful in the practice of the invention. Accordingly, a preferred example of the invention involves providing a homocysteinase to contain one or more peptide (sub)sequences of SEQ ID NO:10 that are selected from the group consisting of:

(a) Gly-Gly-Asn-Arg-Leu-Ala-Gly-Gln-Glu, (see residues 43–51 of SEQ ID NO:10);
(b) a subset of (a) that comprises Leu;
(c) Arg-Val-Cys-Lys-Glu-Ala-His-Ser-Gln, (see residues 168–176 of SEQ ID NO:10);
(d) a subset of (c) that comprises Glu;
(e) Gln-Met-Arg-Met-Tyr-Gly-Ser-Met-Ile; (see residues 304–312 of SEQ ID NO:10); and
(f) a subset of (e) that comprises Tyr.

It should also be noted that SEQ ID NO:10, a preferred homocysteinase of the invention, is expressed from a DNA sequence (pAC2-1, see SEQ ID NO:9) isolated as a gene from *Trichomonas vaginalis* genomic DNA. In contrast, the reported isolation of mgl1 and mgl2 appears to have involved a cDNA procedure. pAC2-1 may thus represent a new homocysteinase Trichomonas gene.

In a representative example, the homocysteinase is patterned on an enzyme from Pseudomonas, Clostridium, Aeromonas or Trichomonas wherein one or more peptide (sub) sequences of the original polypeptide sequence(s) thereof are correspondingly replaced by one or more homologous peptide sequences of SEQ ID NO:10 that are selected from the group consisting of:
(a) Gly-Gly-Asn-Arg-Leu-Ala-Gly-Gln-Glu, (see residues 43–51 of SEQ ID NO:10);
(b) a subset of (a) that comprises Leu;
(c) Arg-Val-Cys-Lys-Glu-Ala-His-Ser-Gln, (see residues 168–176 of SEQ ID NO:10);
(d) a subset of (c) that comprises Glu;
(e) Gln-Met-Arg-Met-Tyr-Gly-Ser-Met-Ile, (see residues 304–312 of SEQ ID NO:10); and
(f) a subset of (e) that comprises Tyr.

In this regard, use of the term "homologous" is not intented to suggest that such homology is exact, but rather, that a comparison of such sequences using generally recognized models would suggest that such sequences, even if now signficantly different, may have evolved from a common ancestor gene or subset thereof. Similarly, the term "mutation" as used herein, should be broadly understood to include modifications that arise by whatever means, whether natural, or experimental and the like.

Accordingly, a generally preferred example includes a chimeric homocysteinase patterned on a first Trichomonas homocysteinase wherein one or more amino acids thereof, that correspond to the Leu$^{47}$, Glu$^{172}$, and Tyr$^{308}$ residues of a second Trichomonas homocysteinase (that from pAC2-1, as depicted in SEQ ID NO:10), are correspondingly replaced by one or more of said Leu$^{47}$, Glu$^{172}$, and Tyr$^{308}$.

An additional example of the invention is defined by a homocysteinase that is a substitution variant, addition variant, deletion variant, or other derivative of SEQ ID NO:10, wherein said variant or derivative has one or both of the following properties:
(a) at least about 10%, preferably about 25%, more preferably at least 50% of the activity of SEQ ID NO:10 toward homocysteine in a suitable assay (such as described in Example 8); and/or
(b) no more than about 1000%, preferably less than 500%, more preferably less than 200% of the activity of SEQ ID NO:10 toward cysteine or methionine in a suitable assay (such as described in Example 8).

Such a range of properties is generally believed to maintain sufficiently enhanced activity of the enzyme with respect to homocysteine, in comparison with cysteine or methionine, that single step methodology is still practical, although it will be appreciated that the exact requirements for such relative sensitivity may be readily determined in each clinical application. For example, cysteine would generally be expected to be at low concentration in a urine sample, at least with respect to a non-diseased patient. With respect to the provision of mutant homocysteinases from other organisms, as produced for example by appropriate recombinant methods, the above relative guidelines are expected to prove useful. The enzyme represented by SEQ ID NO: 10 is a particularly useful example given that the apparent activity of this homocysteinase for homocysteine is at least about 100-fold greater than for cysteine and methionine.

In a representative example whereby a homocysteinase is modified to improve its usefulness for single-step assay methodology, the wild type *T. vaginalis* amino acid sequence (from mgl1, see SEQ ID NOS: 11 and 12) is altered (generally of course by modification of an appropriate encoding DNA) as follows:
one or more of Phe$^{47}$, Asp$^{172}$, and Ser$^{308}$ thereof is deleted, or is replaced according to the following formula:
(1) for Phe$^{47}$, replace with Leu, Ile, Val, Ala, Gly, Met, and Trp;
(2) for Asp$^{172}$, replace with Glu, Gln, or Asn;
(3) for Ser$^{308}$, replace with Tyr, Phe, Met, Trp, Gln, Thr, or Asn,
wherein are suggested relatively conservative amino acid substitutions, as is recognized in the art, and whose efficacy in this regard can be determined by routine experimentation.

As further described below (see Example 7), nickel-NTA affinity purification procedures (available from the Qiagen Company, Germany) can be used to facilitate purification of homocysteinase from *E. coli* or other host cells transfected with an appropriate homocysteinase-encoding DNA sequence. These procedures take advantage of the selective binding of protein imidazole groups to nickel cations immobilized in the NTA resin matrix. In a preferred example of this aspect of the invention, by modification of an appropriate encoding DNA (see SEQ ID NOS: 9 and 10), an amino terminal tag that contains, for example, 6 consecutive histidine residues is introduced into the homocysteinase, thereby facilitating its purification from host cell materials.

Homocysteinease SEQ ID NO: 10 (see also FIG. 1AB), is representative of modified homocysteinase enzymes that comprise one or more histidine residues positioned on the N-terminal side of the natural Met$^1$ of said proteins, said modified enzymes being sufficiently non reactive toward cysteine or methionine that the concentration of homocysteine that is present in a sample of tissue fluid, urine, blood, blood serum, or blood plasma of a subject may be determined by use of such enzymes in a single step assay. In such an assay, the amount of one or more products resulting from reaction of said modified homocysteinease on homocysteine are measured, and such measurements are substantially unaffected by the concentration of cysteine or methionine in the sample. According to this aspect of the disclosure, a homocysteinase that is useful in the practice of the invention comprises one or more, preferably 2–15, and most preferably 5–8 histidine residues consecutively positioned on the N-terminal side of the natural homocysteinase Met$^1$.

EXAMPLES

Example 1

Detection of Homocysteine by Double Enzymatic Subtraction in a Sample Containing Cysteine The concentration of free homocysteine in a blood plasma sample is determined as follows. Blood samples (0.1 to 5.0 mL) are collected with a standard vacutainer using EDTA as anticoagulant, and plasma is then prepared by centrifugation.

While it is expected that measurement of free homocysteine in biological samples provides the clinician with useful predictive information, it is recognized that a large fraction of homocysteine exists disulfide bonded to other molecules (for example, free cysteine, other homocysteine molecules, and available protein sulfhydryl groups). According to the practice of the invention, it is generally preferred to use a disulfide reducing agent (such as dithiothreitol, "DTT") in a protocol to permit detection of the broader pool of homocysteine molecules.

A stock homocysteinase solution of 150 units/ml *Trichomonas vaginalis* enzyme is also prepared. Stock solutions of enzyme generally range from 1–1000 units/ml, and preferably 100–200 units/ml, although the exact activity is subject to selection by the practitioner, depending on various factors, including the concentration of homocysteine in the samples.

As described above, use of *P. putida* enzyme is also preferred, at similar activity levels.

The plasma sample, at an appropriate dilution in buffer, is divided into two equal volumes, Parts 1 and 2. To Part 1 is added a suitable amount of S-adenosylhomocysteine hydrolase ("SAHH") and also a quantity of adenosine (SAHH is available from both eukaryotic and prokaryotic sources, and a procedure for cloning it in *T. vaginalis* has been presented, Bagnara et al. *Molecular and Biochemical Parasitology,* 81, pp.1–11, 1996). In the presence of sufficient adenosine, the plasma homocysteine is converted to S-adenosylhomocysteine. The Part 2 volume is not reacted with SAHH.

*Trichomonas vaginalis* homocysteinase is then added to the Part 1 and Part 2 samples and reacted for about 10–30 minutes. A final concentration of homocysteinase in the range of 0.5–1 unit/mL is preferred, although the exact amount may be adjusted as needed. It is noted that the adenosine remaining in the Part 1 sample prevents the hydrolyase reaction from running in reverse, and so its initial concentration should be chosen with this in mind. The amount needed may depend on the SAHH selected, but a useful starting point is a concentration not less than that of the homocysteine present. Hydrogen sulfide is then measured in both Part 1 and Part 2, and the amount of homocysteine present in the original sample is calculated by subtracting the hydrogen sulfide measurement of part 1 from that of part 2, and doubling the result. The hydrogen sulfide measurement is performed by adding lead acetate to the samples in the range of about 0.1 to 1.0 Molar, thus precipitating the sulfide. The precipitate is measured in a standard spectrophotometer at 360 nm, or other suitable wavelength (such as in the visible range) at which the insoluble precipitate can be determined. This procedure is readily automated.

An additional enzyme useful in the practice of the double enzymatic subtraction approach is cystathionine β-synthase, which catalyzes production in the body of cystathionine from homocysteine and serine. For blood serum or plasma samples, the reaction may be driven in the direction of cystathionine by taking advantage of the relatively high concentration of serine in the blood. Suitable sources of this enzyme include material isolated from Trichomonas, from Pseudomonas, or from mammalian tissues including, for example, liver. The enzyme may be used in an amount that provides a units/ml equivalent to the range described above for S-adenosylhomocysteine hydrolase. As mentioned above in connection with the use of SAHH, it is preferable that steps be taken to prevent this enzymatic reaction from running backwards, which may lead to inaccurate data. The reaction may be driven, and then maintained, in the direction of cystathionine by adding exogenous serine to the reaction samples, or by irreversibly inhibiting the enzyme once conversion to cystathionine has been accomplished. Suitable inhibitors include serine analogs of high affinity for the active site.

A further additional procedure based on the double enzymatic subtraction approach may be available. Recent published work may indicate that the enzyme methionine tRNA synthetase (methionine tRNA synthase) is capable of accepting homocysteine as a reactant (see H. Jakubowsky et al., *FEBS Letters,* 317, pp. 237–246, 1993). Thus it may be possible to reproduce the above result using this enzyme.

Example 2

Alternate S-adenosylbomocysteine Hydrolase Procedure

S-adenosylhomocysteine produced according to Example 1 is subjected to the following manipulations: following its production it is isolated, and contacted with a further amount of S-adenosylhomocysteine hydrolase under conditions where S-adenosylhomocysteine is converted back to homocysteine; after which the homocysteine so produced with said enzyme preparation is contacted with homocysteinase to produce hydrogen sulfide therefrom.

Example 3

Detection of Homocysteine by a Direct Enzymatic Subtraction in a Sample Containing Cysteine Following the initial procedures of Example 1, a blood plasma sample containing both homocysteine and cysteine is prepared. The sample is not divided into parts; instead, a sample of the enzyme cysteine tRNA synthetase is added under conditions that cysteine present is combined with tRNA. The enzyme selected may be of eukaryotic or prokaryotic origin, and conditions for its reaction are well known in the art.

The cysteine-depleted sample is then reacted with homocysteinase as aforementioned, and the homocysteine concentration is determined directly from the hydrogen sulfide measurement.

An additional example of the direct enzymatic subtraction method is provided below in Example 10, and is based on the enzyme γ-glutamylcysteine synthetase which may be of eukaryotic or prokaryotic origin. Assay systems that incorporate use of this enzyme are described.

Additional enzymes useful to deplete cysteine include cysteine oxidase and cystathionine β-synthetase.

Example 4

Methods to Detect Homocysteine Bonded to Other Biomolecules

As aforementioned, homocysteine exists in biological fluids bonded to other biomolecules, and homocysteine "stored" in such forms is believed to contribute to pathological processes. Thus it is desireable to determine total homocysteine, and this includes (1) homocysteine dimers, (2) homocysteine/cysteine heterodimers, (3) conjugates of homocysteine and protein wherein homocysteine is attached by way of disulfide bonds to protein cysteine, and also (4) conjugates of homocysteine and protein wherein homocysteine (including N-Acylated forms thereof) is bonded to protein amino acid R groups, most notably to the epsilon amino group of protein lysine.

With respect to forms (1) through (3), reducing solutions are used to release the covalently bound homocysteine. In one example, a stock sodium borohydride or sodium cyanoborohydride solution is prepared at about 0.1 M or less. The reaction is carried out by adding the borohydride to the plasma sample (prepared following the intitial procedure of Example 1) at pH 6 to 8 for 5–10 minutes at room temperature. The excess borohydride is destroyed, and the sample may then be subjected to the enzymatic procedures of Examples 1 or 3. Alternatively, the borohydride may be neutralized with HCl if the sample is further manipulated according to the following procedure.

It has been found, however, that sodium borohydride can denature homocysteinases under certain circumstances, so use of DTT is preferred.

Example 5

Manipulations Under Acid Conditions

With respect to form (4) above, 6 N HCl can be used by dilution at about 50/50 with the protein sample. Following reflux at boiling temperature for 1–2 hours under nitrogen, water is removed from the sample under vacuum to complete dryness. This liberates homocysteine if bonded to other amino acids, and also completes the homocysteine lactonization process. At the point of dryness, sodium acetate (1M) and acetic anhydride (10M) are added. This is refluxed for one further hour at boiling temperature to create acetylated homocysteine thiolactone.

The anhydride is removed by evaporation to dryness. The N-acetylated homocysteine thiolactone is selectively extracted with ether. The ether is then evaporated at 35 degrees C under vacuum. Physiologically buffered water (phosphate buffered saline, pH 7.5) is then added which then opens the thiolactone ring. At this point, either of two reactions is carried out. Homocysteinase may then be added and reacted for 10–30 minutes followed by detection of hydrogen sulfide as above, or preferrably a hog-kidney deacetylase is added to deacylate the homocysteine with subsequent addition of the homocysteinase.

Example 6

Additional Methods for Detection of Homocysteine by a Direct Enzymatic Subtraction in a Sample that also Contains Cysteine Generally speaking, this additional method takes advantage of the fact that pyruvate produced from cysteine by the action of homocysteinases may be detected independently of the hydrogen sulfide that is generated by the action of homocysteinases on both homocysteine and cysteine present in biological samples, such as blood plasma. Thus determination of homocysteine may be made by simple subtraction. According to this method, pyruvate can be determined enzymatically by any number of enzymes that generate a detectable product therefrom. Similarly, α-ketobutyrate (produced from homocysteine but not cysteine) can be determined in relation to hydrogen sulfide using leucine dehydrogenase.

The two principal processes of the method, detection of pyruvate and detection of hydrogen sulfide, may be conducted simultaneously in a single sample, or they may be conducted separately in parallel samples, in either case with appropriate controls.

In a preferred example, the enzyme used to detect pyruvate is a mammalian lactate dehydrogenase, and determinations of both pyruvate and total hydrogen sulfide are performed in a single cuvette, using a standard spectrophotometer. Following the initial procedures of Example 1, a blood plasma sample containing both homocysteine and cysteine is prepared. The sample is not divided into parts, instead a sample of a homocysteinase (from *Trichomonas vaginalis* or *P. putida*) is added under conditions such that hydrogen sulfide, ammonia, and α-keto butyrate are produced from homocysteine, and additionally, hydrogen sulfide, ammonia and pyruvate are produced from cysteine. A sample of the enzyme lactate dehydrogenase (at an amount of units/ml comparable to that used in previous examples) is also added under conditions such that it will react with the pyruvate produced from cysteine, which reaction is then monitored at or in the vicinity of 340 nm (for NADH), per well known procedures.

The total concentration of both homocysteine and cysteine in a sample may be determined colorimetrically, as before (see Example 1), by measuring the total hydrogen sulfide produced from homocysteinase, and at any suitable wavelength at which the precipitating colored lead salt can be detected, such as in the visible range, or also at or near, for example, 360 nm. Hydrogen sulfide may also be detected based on formation of other chromophoric metal salts, as is known in the art. The homocysteine concentration in the original sample is determined by comparison of the total hydrogen sulfide produced (from cysteine and homocysteine) with the total pyruvate produced (from cysteine only). This procedure is also readily automated, and both detection wavelengths can be monitored simultaneously.

Although use of lactate dehydrogenase to detect pyruvate in blood, or in solutions derived from blood, may follow one of several art-recognized procedures, certain precautions should be repeated. Pyruvate is very unstable in blood, and in materials derived therefrom, and it may even polymerize. Accordingly, it may be desirable to conduct pyruvate determinations on protein-free filtrates of recovered samples, and on such samples only when processed with metaphosphoric acid, as is known in the art.

Example 7

Production of the *E. coli* BL21 (DE3) pAC2-1 clone

The cloning of the pAC2-1 homocysteinase gene of *Trichomonas vaginalis* was accomplished as described below. Generally speaking, recombinant methodology recognized as applicable in other microorganisms is useful with respect to manipulation of Trichomonas DNA, particularly so since many Trichomonas genes, as aforementioned, lack introns. Useful reference may therefore be made to Y. Tan et al., *Protein Expression and Purification*, 9, pp. 233–245, (1997) and International Patent publication number WO 96/40284 of Y. Tan et al., published Dec. 19, 1996.

Genomic DNA from *Trichomonas vaginalis* was isolated by standard procedures (Wizard Minipreps, Promega, Madison, Wis.), and used as a template for a PCR reaction conducted according to the method provided with a PCR reagent kit (Roche, Branchburg, N.J.). Oligonucleotide primers were developed based on the nucleotide sequence of the mgl1 gene (J. C. Mottram et al., *Gene Bank*, accession number AJ000486, NID g2330884, submitted Jul. 17, 1997).

The specific primers used were:
(sense)
5'-GGATTACATATGCATCATCATCATCATCACATGA GTGGCCACGCTATCGAC-3' (SEQ ID NO:13), which includes a CATATG NdeI site; and (antisense) 5'-GGATTAGGATCCTTAGAGGACTAAGTCGAGAG CC-3' (SEQ ID NO:14), which includes a GGATCC BamHI site. Additional reagents used included restriction endonucleases, T4 DNA ligase, and BL21(DE3) competent cells, all purchased from Stratagene (San Diego, Calif.). The GeneAmp PCR reagent kit was purchased from Roche (Branchburg, N.J.), and the DNA purification kit was purchased from Promega (Madison, Wis.). The oligonucleotide probes for PCR amplification were synthesized by IDT Inc. (Coralville, Iowa). All other reagents were purchased from Sigma (St. Louis, Mo.). Wild type *Trichomonas vaginalis* was purchased from the American Type Culture Collection (Rockville, Md.).

The PCR reaction conditions were as follows: 35 cycles of denaturation at 94° C. for 1 minute; annealing at 50° C. for 2 minutes; and extension at 72° C. for 2 minutes. This was followed by a final extension step at 72° C. for 10 minutes. The PCR-amplified product (which appeared as one band of 1.2K bp identified by Kb-ladder markers) was collected, digested with the NdeI and BamHI restriction enzymes, and then ligated into the pT7-7 vector at the NdeI and BamHI cloning sites thereof, using standard protocols (the pT7-7 vector was provided by Dr. Stan Tabor, Harvard Medical School, Boston, Mass., see Tabor, S. "Expression using the T7 RNA polymerase/promoter system," in *Current Protocols in Molecular Biology*, F. A. Ausubel, et al., eds., 1990, pp. 16.2.1–16.2.11, Greene Publishing and Wiley-Interscience, New York). The resulting plasmid was then transformed into *E. coli* BL21 (DE3) cells by electrotransformation.

After incubation at 37° C. overnight, ampicillin-resistance clones were selected from ampicillin-containing plates. The cells from the selected colonies were grown in 5 ml LB medium (Fisher) at 37° C. overnight. Suitable clones were selected based on enzyme activity of crude culture extracts in the α-ketobutyrate assay (using a modification of the method of K. Soda et al., *Methods in Enzymology*, 143, 459–465, 1981—based on reaction of methyl-2-benzothiazolinone hydrazone), and/or a dethiomethylation assay in which $H_2S$ is produced and quantified (see A. E. Braunstein et al., *Biochimica et Biophysica Acta*, 242, pp. 247–260, 1971), which are both recited directly below.

A variant of the *E. coli* BL21 (DE3) pAC2-1 clone was also constructed which differs only in that the included plasmid (expression vector pAC2-11, again based on pT7-7) contains two copies of the homocysteinase-encoding sequence, which are present in tandem. This particular clone, designated *E. coli* BL21 (DE3) pAC2-11 provides high level expression of recombinant homocysteinase for use in the diagnosis procedures of the invention. Briefly the 2 copies of the encoding sequence were placed between the NdeI and Bsp106I sites of pT7-7. The first copy was linked NdeI to BamHI, and the second was linked BamHI to Bsp106I. Recombinant homocysteinase may be purified from either the pAC2-1 or pAC2-11 clones by the same procedures.

The α-ketobutryate/pyruvate Assay

In the first step of this assay, 1 ml volumes of 100 mM phosphate buffer pH 8.0, containing also 10 μM pyridoxal phosphate, and different concentrations (25 μM–25 mM) of DL-homocysteine, or L-methionine, or L-cysteine, respectively, were incubated, for 10 min at 37° C., with a sufficient sample (typically 50 μl) of crude cell extract (cells were sonicated, and the supernatant was recovered following centrifugation) to provide about 1–100 units of homocysteinase ("HCYase") enzyme. The reactions were stopped by adding 0.1 ml of 50% TCA. The suspensions were then centrifuged using an Eppendorf centrifuge at 13k rpm for 2 minutes. 0.5 ml samples of the supernatants were then added to 0.5 ml of 0.05% 3-methyl-2-benzothiazolinone hydrazone ("MBTH") in 0.8 ml of 1M sodium acetate, pH 5.2 and incubated at 50° C. for 30 min. The amount of reaction products was determined for each sample, by spectrophotometry at $OD_{320}$. The amount of protein was determined with a Bio-Rad 500-0006 kit (Bio-Rad, Richmond, Calif.) with bovine serum albumin as a standard. The enzyme specific activity was calculated as units/mg protein, with one unit of enzyme defined as the amount that catalyzes the formation of 1 μmol of α-ketobutyrate from homocysteine per minute. The assay procedure can, of course, also be used with purified homocysteinase samples that provide, for example, 1–100 units of enzyme per assay test.

The Dethiomethylation Screening Assay

As aforementioned, the assay used was a modification of the method of A. E. Braunstein et al. above. The standard reaction mixture consisted of potassium phosphate buffer (pH 7.5, 100 mM), lead acetate (0.33 mM), and sufficient crude cell extract to provide 1–100 units of homocysteinase, to which mixture different concentrations (5 μM–100 μM) of substrate DL-homocysteine, or L-cysteine or L-methionine were added, such that the total reaction volume was 1.5 ml. After incubation at 37° C. for 10 min, the determination of lead sulfide was obtained on a spectrophotometer at $OD_{360}$. The assay procedure can also be used with purified homocysteinase samples, for example, those providing 1–100 units per assay test.

Purification of Product Homocysteinase

Figure 3:
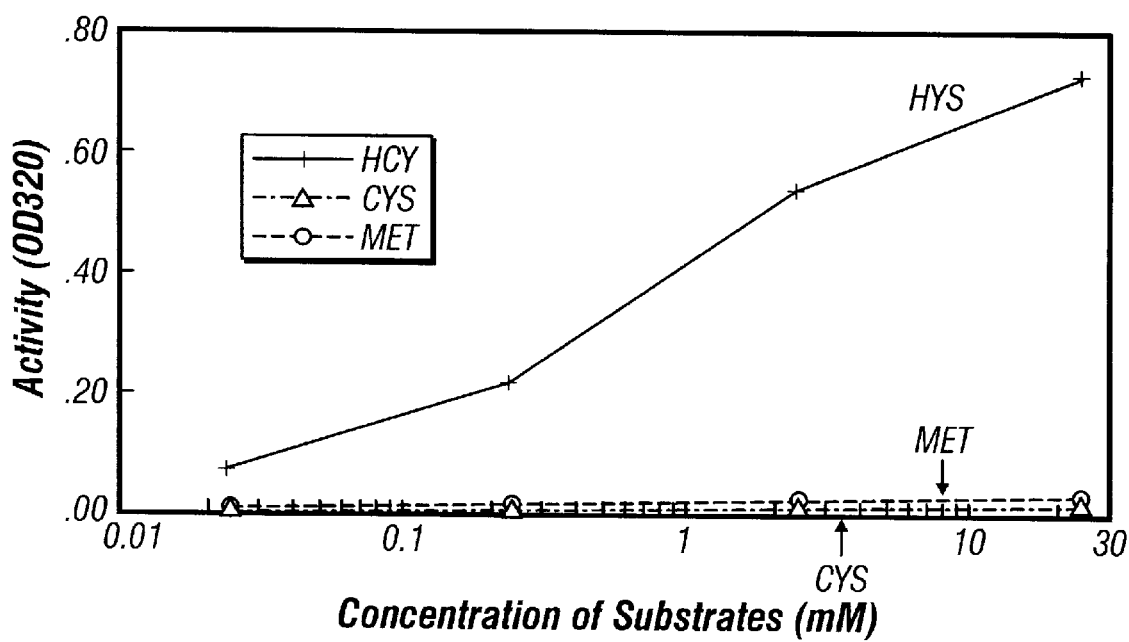
FIG. 3 shows the comparative specific activities of homocysteinase (pAC2-1 clone, purified using a DEAE-Fast Flow procedure) for cysteine, methionine, and homocysteine.
Figure 4:
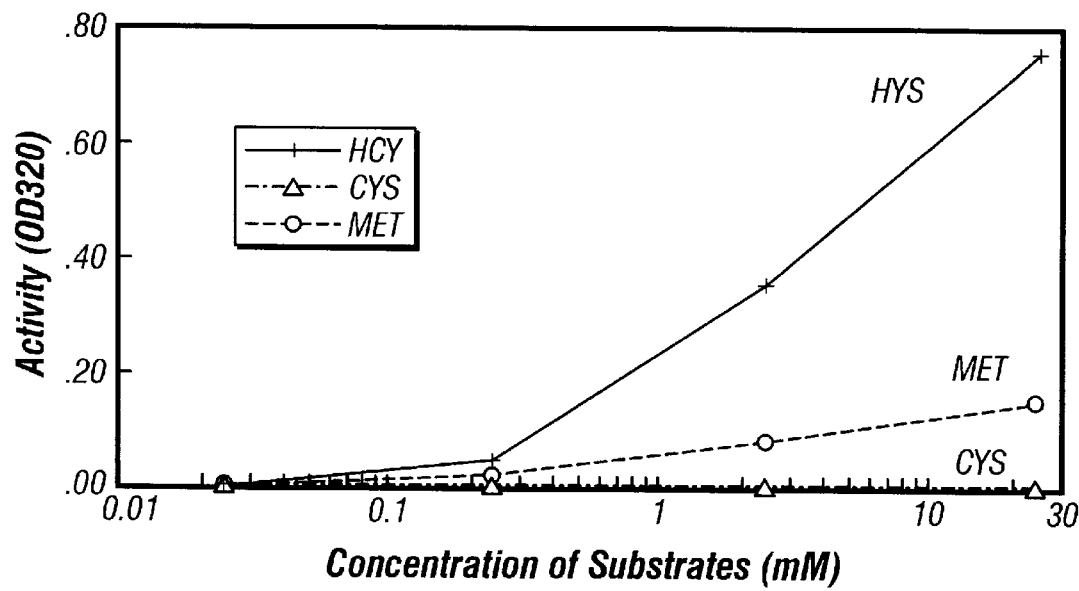
FIG. 4 shows the comparative specific activities of homocysteinase (pAC2-1 clone, purified using a nickel cation affinity reagent) for cysteine, methionine, and homocysteine.

Following use of the above initial assay screens, homocysteinases ("HCYases") from promising clones were purified using protocols that included DEAE Sepharose Fast Flow chromatography (for resultant enzyme activity profiles from the pAC2-1 clone, see FIG. 3), or included nickel-NTA affinity chromatography (for resultant enzyme activity profiles from the pAC2-1 clone, see FIG. 4).

Cell Growth Conditions

10 μl of frozen *E. coli* stock corresponding to a particular clone was seeded into 5 ml LB medium (Fisher) containing also 10 g/ml ampicillin, and cultured overnight at 30° C. with moderate shaking (300 rpm). The culture was then divided into 2 fresh 100 ml volumes of LB medium in 500 ml flasks, and further cultured at 30° C. for 6 hours, also at 300 rpm. The entire culture was then divided into 18 flasks (each of 6 liters) containing 800 ml of LB medium. Growth was continued, overnight, at 37° C. at 300 rpm and an $OD_{600}$ of approximately 10 was achieved. The bacteria were then spun down at 4000 g permitting replacement of the growth medium with fresh LB, and the incubation was continued for a further 6 hours, again at 37° C. and 300 rpm. When the $OD_{600}$ reached 20, the bacteria were harvested by centrifugation for 10 minutes at 4000 g, 4° C. It will be recognized that a wide variety of variations on the above procedure are also effective.

Pre-treatment Prior to Chromatography

The bacterial pellet was first suspended in extraction solution (20 mM potassium phosphate, 10 μM pyridoxal phosphate and 0.01% β-mercaptoethanol, pH 9.0), and the cells were then disrupted with a cavitator-type homogenizer (model HC 8000, Microfluidics Corporation, Newton, Mass.). The suspension was centrifuged with a refrigerated centrifuge (Sorvall, superspeed RC2-B) at 8000 g, 4° C. for 30 minutes. The supernatant was then collected, heated at 50° C. for 1 minute, and then subject to ultrafiltration using a preparative scale device (model TFF PLHK 100k, Millipore, Bedford, Mass.) using a 2.5 ft$^2$ pressure cartridge containing 10 mM potassium phosphate buffer, pH 8.3). The pH was adjusted to 7.2 during the ultrafiltration.

Chromatographic Conditions-First Column

The above-derived concentrate (at pH 7.2) was applied to a first column (100 mm diameter×30 cm) containing a 2400 ml packed volume of DEAE Sepharose® FF (Pharmacia, Uppsala, Sweden) in 40 mM KCl-PPM buffer (40 mM potassium chloride; and 10 mM potassium phosphate, 10 μM pyridoxal phosphate, 0.01% β-mercaptoethanol, pH 7.2). After loading the protein sample, the column was pre-washed with about 10 volumes of 40 mM KCl-PPM buffer until the $OD_{280}$ dropped below 0.1. The protein was then eluted with a linear gradient of 40–300 mM KCl in PPM buffer, and 500 ml fractions were collected. The fractions containing homocysteinase were identified by their yellow color, and an activity assay.

Chromatographic Conditions-Second Column

Following a 24 hour dialysis period against a solution of 80 mM KCl, 10 mM potassium phosphate, pH 8.3, the recovered eluate (about 2–5 mg/ml representing a recovery of 5–10 total grams protein) was applied to a second column. After loading, the second column (Pharmacia XK 50/30 filled with DEAE Sepharose® FF—500 ml volume, 50 mm diameter×25 cm) was pre-washed with 4 volumes of 80 mM KCl, 10 mM potassium phosphate, pH 8.3 (at a flow rate of about 6–8 ml/minute) until the $OD_{280}$ dropped below 0.1. The homocysteinase was then eluted with a linear gradient of 80 to 300 mM potassium chloride in 10 mM potassium phosphate buffer (pH 8.3). Eluate was collected in 300 ml fractions, and active fractions were identifiable by yellow color and homocysteinase enzyme activity. Enzyme activity results (toward homocysteine, cysteine, and methionine) for homocysteinase purified in this manner are discussed in Example 8 below (see also FIG. 3).

Alternatively, an additional two stage strategy may be used. In the first stage, the partitioning material was DEAE Sepharose® FF, and loading and pre-washing were conducted with 20 mM sodium phosphate buffer, pH 7.2. Elution of the protein was accomplished using a linear gradient (8 ml/min) from 20 mM sodium phosphate buffer, pH 7.2 (solution A) to 20 mM sodium phosphate buffer, pH 7.2, 500 mM NaCl (solution B). In the second stage, the partitioning material was phenyl Sepharose® 6-FF, and loading and pre-washing were conducted with 0.6 M $NH_4SO_4$ in 20 mM sodium phosphate buffer, pH 7.2. Elution of the protein was accomplished using a linear gradient (5 ml/min) from 0.6 M $NH_4SO_4$, 20 mM sodium phosphate buffer, pH 7.2 (solution A) to 20 mM sodium phosphate buffer, pH 7.2, (solution B). The following purification results were obtained for this alternate procedure. The above-described cell-lysate contained 8400 units of homocysteinase at a specific activity (units/mg) of 5.2. Following completion of pre-column procedures, 6,300 units were recovered at a specific activity of 64 (about 75% yield). Upon completion of the DEAE Sepharose®-FF step (first column), 5,040 units were recovered at a specific activity of 172 (60% yield), while after the phenyl Sepharose® 6-FF step (second column), 4,200 units remained at a specific activity of 300 (50% yield).

Analysis of Resultant Homocysteinase

For HPLC analysis, an L-6200A Intelligent pump (Hitachi, Ltd., Tokyo, Japan) with a Supelco Progel™ TSK column (G3000 $SW_{XL}$, 30 cm×7.8 mm, Supelco, Bellefonte, Pa.) was used. Typically samples of a 20 μl size (containing about 0.1 to 0.5 mg/ml protein were loaded, and eluted with a solution of 0.12 M NaCl, 10 mM sodium phosphate buffer, pH 7.2, at a flow rate of about 1 ml/min. The protein containing fractions were identified with a spectrophotometer (Hitachi U2000) at a wavelength of 280 nm. Bovine serum albumin (MW 66,000) and β-amylase from sweet potato (MW 200,000) (Sigma, St. Louis, Mo.) were used as MW standards. Resultant retetion times were: for BSA, 8.88 min; for β-amylase, 7.82 min; and, for the product homocysteinase, 8.28 minutes.

Electrophoresis of resultant proteins was carried out on (non-reducing) 7.5% or 10% polyacrylamide-precasted plates in 0.2 M Tris-glycine buffer, pH 8.3, with and without 0.1% SDS. The molecular weight standards used were the Kaleidoscope Prestained Standards (Bio-Rad, Richmond, Calif.). The product homocysteinase resolved as a single band of about 43 kD in the presence of 0.1% SDS, and as a single band at about 172 kD absent 0.1% SDS.

DNA sequencing of suitable clones was then performed by ACGT Inc. (Northbrook, Ill.) using T7 DNA polymerase and the dideoxy nucleotide termination reaction. The primer walking method was used, and the sequences were analyzed on a DNA analyzer.

Purification of Homocysteinase as a 6× Histidine-Tagged Protein using Ni-NTA Methodology An alternate method to purify recombinant homocysteinase from *E. coli* involves use of nickel-NTA affinity chromatography. This technology takes advantage of the affinity of protein histidine imidazoles for nickel cations immobilized in the NTA resin matrix. In order to take full advantage of this technology (Qiagen Company, Germany), a sequence of 6 additional histidine residues is added (preferably by modification of an encoding DNA which is then expressed) to the protein on the N-terminal side of the natural Met[1] of the homocysteinase (see Example 7 above, and SEQ ID NOS 9 and 10).

According to this purification procedure (for additional information, see also "The QIAexpressionist, A handbook for high level expression and purification of 6×His-tagged proteins" March 1997, 3rd edition, available from Qiagen) 100 ml of densely grown culture of *E. coli* BL21 (DE3), clone pAC2-1 were harvested by centrifugation, and the resultant pellet was resuspended in 4 ml lysis buffer (300 mM NaCl, 10 mM imidazole, 50 mM $NaH_2PO_4$, pH 8.0). The resultant cell suspension was then sonicated on ice for one minute.

Cellular debris was removed using a benchtop centrifuge set at maximum speed for 20 minutes. The clear supernatant was then mixed with 1 ml of Ni-NTA slurry (Qiagen), and gently shaken on ice for 60 minutes to allow adsorption. The mixture was then transfered to a disposable polypropylene column and the flowthrough fraction was discarded. The Ni-NTA resin beads were then washed with 8 ml of wash buffer (300 mM NaCl, 20 mM imidazole, 50 mM $NaH_2PO_4$, pH 8.0), after which the recombinant protein was finally collected by elution using 2 ml of elution buffer (300 mM NaCl, 250 mM imidazole, 50 mM $NaH_2PO_4$, pH 8.0). The purified protein was then characterized as above. Enzyme activity results (toward homocysteine, cysteine, and methionine) for homocysteinase purified in this fashion are described in Example 8 below (see also FIG. 4).

Example 8

Representative Catalytic Properties of the Homocysteinases of the Invention

FIGS. 2 through 4 evidence the significantly enhanced usefulness of the homocysteinases of the invention for single step assays. The results depicted in FIG. 2 reflect use of a crude lysate of the host E. coli cells containing the pAC2-1 clone, and show specific activity (u/mg) with respect to the 3 substrates (homocysteine, methionine, and cysteine) when each is present in a separate assay at 25 mM. The results depicted in FIGS. 3 and 4 (again for E. coli containing the pAC2-1 clone) reflect relative activity of purified enzyme preparations for homocysteine, methionine, and cysteine. For the assays shown in FIG. 3, the enzyme was purified using a DEAE Sepharose Fast Flow procedure as described in Example 7; for FIG. 4, the purification procedure of Example 7 involving nickel-NTA agarose affinity reagent, was used (see above under the heading "The α-ketobutyrate assay/pyruvate assay" for methodology).

It is well recognized that numerous procedures are available to purify recombinant homocysteinases from host E. coli cells. As exemplified, the novel homocysteinases of the invention exhibit activities toward homocysteine (using the assays of the invention, see for example, Example 1) that are typically 100-fold, and even up to about 1000-fold, higher than their activities exhibited toward cysteine or methionine.

Example 9

Single Step/Single Enzyme Clinical Assays

It will be immediately recognized that procedures for multi-step/multi-enzyme assays of homocysteine in biological fluids are readily adapted for use in simplified single step/single enzyme assays in order to take advantage of the substrate specificity of novel species of homocysteinase (the terms "single step assay" and "single enzyme assay" are used interchangeably herein to indicate that the biological sample need only be contacted with one enzyme in order to accurately measure homocysteine in the presence of cysteine, and/or methionine). The concentrations of homocysteinase appropriate for such procedures are broadly equivalent those described above in Example 1, or elsewhere in the Specification, or are readily determined.

According to the single-enzyme diagnostic methods of the invention, the concentration of homocysteine in a biological sample such as, for example, whole blood, blood plasma, serum, urine, or tissue fluid may be determined with sufficient accuracy to provide valuable diagnostic information to physicians, absent interference from contaminating concentrations of cysteine and/or methionine. Such diagnostic assays are rapid, accurate, involve a minimum of reagents, and are therefore applicable to large scale screenings operations in clinical laboratories, and as public health measures.

In a representative example, the concentration of cysteine in normal blood plasma may be about 30–120 μM (micromolar), and that of homocysteine only about 5–15 μM. As is recognized in the art, a subject's risk for cardiovascular disease may increase significantly as homocysteine concentrations in the blood plasma rise above the 15 μM level. High risk cardiovascular patients have been identified that have homocysteine levels up to several hundred micromolar. Similarly, patients affected by disorders of cysteine metabolism may have cysteine levels up to 500 or even 1000 μM. The diagnostic kits of the present invention are useful to determine homocysteine concentrations in biological fluids in the range of 1–500 μmolar, for example, wherein said fluids also contain from 0 μmolar (typically from 10 μmolar) to about 1000 μmolar of cysteine, or higher.

According to the preferred practice of the invention, homocysteineases are provided wherein the relative activities of said enzymes toward homocysteine versus cysteine are such that, by detecting product hydrogen sulfide, the apparent concentration of homocysteine measured in a patient sample (which reflects also a contribution from cysteine) is less that about 150%, preferably less than about 110%, and most preferably less than about 102%, of the actual value thereof. In a further prefered example of the invention, for example using the novel Trichomonas homocysteinase expressed from pAC2-1, the apparent concentration of homocysteine measured in a single enzyme assay reflects no more than about a 1% false contribution from cysteine.

According to the practice of the present invention, such single enzyme assay methodology (using for example, SEQ ID NO:10 as homocysteinase) is applicable over a wide range of natural concentrations (and ratios of concentrations) of both homocysteine and cysteine (and also methionine where appropriate), and is thus accurately able to reflect the body fluid chemistry of both healthy subjects and those at risk for disease states, most particulary cardiovascular disease.

Accordingly, in its most preferred aspect, the present invention provides a diagnostic kit for use in the single enzyme assay of the homocysteine concentration in a biological fluid of a subject, said kit comprising:

(a) a homocysteinase enzyme; and
(b) at least one reagent capable of being used to determine the amount of product hydrogen sulfide formed by reaction of homocysteinase on homocysteine; wherein said homocysteinase is sufficiently non-reactive toward cysteine that any hydrogen sulfide produced by reaction of said homocysteinase on cysteine does not substantially interfere with the use of said kit to assess risk for cardiovascular disease.

Since the diagnostic kits of the present invention are useful over a wide spectrum of homocysteine and cysteine concentrations, and relative concentrations, it is to be expected that there are a variety of examples of the successful practice of the invention. Representative examples are as follows:

(1) most generally, the fraction of measured hydrogen sulfide that is attributed to cysteine instead of homocysteine should be sufficiently small to prevent useful interpretation of the results by a qualified medicial practitioner. In general, useful diagnostic information can be obtained when the amount of produced hydrogen sulfide attributable to homocysteine is about one half of the total. Given the generally higher concentration of cysteine in patient samples, compared to homocysteine, the specificity of such enzymes is still evident. Preferably, however the fraction of total hydrogen sulfide detected in an assay that is attributable to homocysteine is at least 90%, preferably 95%, more preferably 98%, and most preferably 99% or greater. The 99% level is readily obtained according to the practice of the invention, for example using the homocysteinase represented by SEQ ID NO:10.

(2) in an assay of a patient sample which evidences risk for cardiovascular disease, wherein the concentration of homocysteine therein is about 20 μmolar or higher, concentrations of 300 μmolar, or even greater, of cysteine contribute less than 1% to the total amount of hydrogen sulfide detected. Obviously such enzymes remain very useful with respect to biological samples having even greater cysteine concentrations.

(3) in an assay of a patient sample which evidences risk for cardiovascular disease, and wherein the ratio of the cysteine to homocysteine concentration is, for example, about 15:1, cysteine contributes less than about 1% to the total amount of hydrogen sulfide detected.

The following further evidences the differences between the properties of known homocysteinases and the novel enzymes of the present invention.

Homocysteinase isolated from *Trichomonas vaginalis* (which may reflect expression from more than one gene) was reported (see Lockwood et al., 1991 above) to have a $K_m$ for homocysteine of about 0.5 mM, whereas $K_m$ values determined for the novel enzyme expressed from the pAC2-1 clone are (all at 37° C., pH 8.0): 4.8 mM, 3.45 mM, and 3.1 mM for homocysteine, cysteine, and methionine, respectively.

Figure 5:
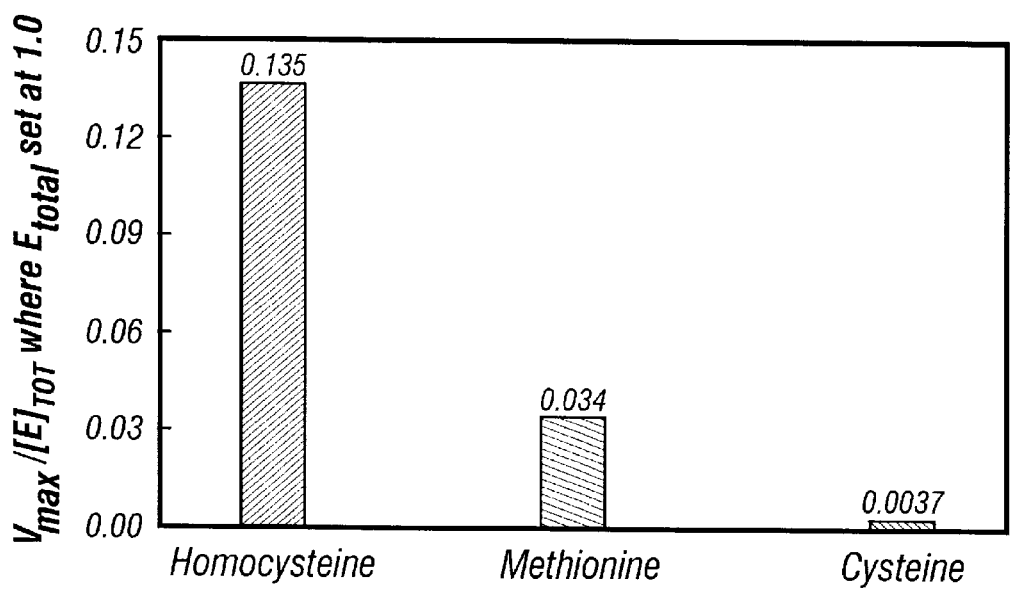
FIG. 5 shows determined $K_{cat}$ values of homocysteinase (pAC2-1 clone) for cysteine, methionine, and homocysteine.

The $K_m$ calculations were determined from assays carried out in one ml volumes of 100 mM phosphate buffer, pH 8.0 containing 10 μM pyridoxal phosphate at different concentrations (10 μM to 1.6 mM) of, separately, DL-homocysteine, L-methionine, or L-cysteine, for 10 minutes at 37° C., pH 8.0 using 50 μl of enzyme (300 units/ml). The reaction was stopped by adding 0.1 ml of 50% TCA. The resultant suspension was then centrifuged with an Eppendorf centrifuge at 13k rpm for 2 minutes. 0.5 ml samples of supernatant were then added to 0.5 ml volumes of 0.05% 3-methyl-2-benzothiazolinone hydrazone in 0.8 ml of 1 M sodium acetate, pH 5.2, and incubated at 50° C. for 30 minutes. The amount of reaction product was then determined by spectrophotometry at $OD_{320}$. The $K_{cat}$ (turnover number) values reported in FIG. 5, were determined from the calculation of $V_{max}$ values using standard kinetic expressions and plots.

It is apparent that the kinetics of the enzyme expressed from the pAC2-1 clone are quite different from those of the wild type enzyme. An additional aspect of the present invention involves recognition that although certain changes have been described in the amino acid sequence of the *T. vaginalis* enzyme in order to provide for enhanced kinetic properties, those skilled in the art will recognize other potential mechanisms to accomplish this. An example thereof is covalent modification of the enzyme, whether or not at the active site. Such other methods of modifying a homocysteinase are within the practice of the invention if they lead to production of an enzyme having kinetic properties such as those first disclosed herein.

Example 10

Assay Technology Based on γ-Glutamylcysteine Synthetase

The enyzme γ-glutamylcysteine synthetase (EC 6.3.2.2, also referred to as glutamate-cysteine ligase) is another enyzme that may be used to enhance accuracy of assays for homocysteine in biological samples. The enzyme catalyzes the first (and rate-limiting) step in the synthesis of glutathione (γ-L glutamyl-L-cysteinylglycine), a tripeptide having numerous important functions in living cells. Given the important roles that glutathione plays in metabolic pathways, it is believed highly unlikely that γ-glutamylcysteine synthetase would accept homocysteine as a replacement for substrate cysteine. Accordingly, use of this enzyme contributes to highly specific determinations of homocysteine in biological samples (via a homocysteinase), by removing any interfering cysteine. In a preferred example, the assay is conducted using the direct enzymatic substraction method (see Example 3 above).

part A—Expression of Encoding DNA for *E. coli* γ-glutamylcysteine Synthetase

A principal achievement of the invention is highly sensitive enzyme-based assay methodology that provides for accurate determinations of homocysteine concentrations in biological samples. As aforementioned, in many kinds of biological samples, naturally occurring concentrations of cysteine interfere with homocysteine determinations. As described below, a particularly preferred enzyme-based assay for homocysteine involves use of two enzymes, (1) a homocysteinase having high specificity for homocysteine and very low specificity for cysteine (such as the *Trichomonas vaginalis* enzyme expressed from pAC2-1, SEQ ID NO: 10), and (2) γ-glutamylcysteine synthetase such as from clone GSH-I His (see below) use of which further eliminates interference from cysteine.

It will immediately be appreciated that once the value of this multienzyme approach is recognized, the γ-glutamylcysteine synthetase enzyme utilized can be provided from a wide variety of sources, such as hog liver, wheat germ, bovine lens, rat liver, or bacteria including *Proteus mirabilis* or *E coli*. B. The γ-glutamylcysteine synthetase enzyme may be purified from such sources by recognized methods, or expressed recombinantly, for example, from host prokaryotic cells such as *E. coli*, or eukaryotic cells generally recognized as useful in this regard. Suitable *E. coli* strains include *E. coli* BL21 (DE3), HB 101, and JM 109.

Given the broad utility of this approach, it will also be immediately apparent that a wide variety of particular assay conditions, enzyme concentrations, detection chromophores, and the like, are available to the clinician based upon the teachings herein. For example, the nucleotide sequence for the *E. coli* B γ-glutamylcysteine synthetase (gsh I)gene has been reported by K. Watanabe et al.(see *Nucleic Acids Research*, 14(11), pp. 4393–4400, 1986, and references cited therein). An open reading frame of 518 amino acids was deduced, and the unusual codon TTG was determined as the translational start ($Met^1$). The enzyme and its function have also been characterized on a molecular level, and expression and purification schemes therefor described (Y. Inoue et al., Applied Microbiology and Biotechnology, 38, pp. 473–477, 1993).

In the practice of the present invention, and in order to clone the *E. coli* γ-glutamylcysteine synthetase gene, genomic DNA for *E. coli* HB 101 was isolated and used as a template for PCR. Primers were selected to permit amplification of the encoding sequence in two overlapping fragments. The primers selected were GSH-1 and GSH-2, corresponding to the smaller resultant gene fragment, and GSH-3 and GSH-4 that were similarly selected for the larger of the fragments. The unusual start codon TTG (see GSH-1, SEQ ID NO: 15 below) was also replaced by an ATG.

The nucleotide sequences for primers GSH-1 through GSH-4 were as follows (the nucleotide numbers are assigned to correspond with those used by K. *Watanabe* et al. at p. 4396, based on an isolated 2098 bp HincII-PstI restriction fragment reported therein that contained the open reading frame):

GSH-1 (sense strand), 5'-ATCGCTAG [CAT <u>ATG</u>$^1$] ATC CCG GAC GTA TCA CAG-3', which includes encoding nucleotides No. 338–358 (K. Watanabe et al.), wherein [CAT <u>ATG</u>$^1$] encodes the Met and provides an NdeI site (SEQ ID NO:15);

GSH-2 (antisense strand), 5'-ATCACCATCC ACTGGTG-TAA TG-3', corresponding to nucleotides No. 541–562 (SEQ ID NO:16);

GSH-3 (sense strand), 5'-CTA CCG ATT TTG CGG AAG-3', corresponding to encoding nucleotides No. 510–527 (SEQ ID NO:17); and GSH-4 (antisense strand), 5'-CATGACGGAT CCTCAG-GCGT GTTTTTCCAG-3', corresponding to nucleotides No. 1877–1894 (1894 is the stop codon), with 12 additional nucleotides attached (SEQ ID NO: 18).

To add an oligo (6-mer) histidine tag at the N-terminus of the resulting protein (compare also Example 7 above), a series of consecutive histidine codons (CAT/CAC) were included at the 5' end of the encoding sequence for primer GSH-1H as follows (GSH-1H was then used in replacement of GSH-1 with GSH-2, and as before, the unusual start codon was replaced):

GSH-1H 5'-ATCGCTAG CAT <u>ATG</u> CAT CAT CAT CAT CAT CAC <u>ATG</u> (original Met[1]) ATC CCG GAC GTA TC-3' (SEQ ID NO:19)

In order to assemble appropriate expression plasmids, the small fragment was digested with NdeI and EcoRI, and the large fragment was digested with EcoRI and BamHI. Both fragments were then used in a 3-way ligation with NdeI/BamHI predigested pT7-7 plasmid which includes Nde I and BamHI sites, to yield the plasmids pGSH-I and pGSH-I-HIS (which differ only in the encoding sequence for the N' end histidine tag). Correct cloning was comfirmed by RE analysis. The plasmids were then transformed into E. coli BL21 (DE3) cells and protein minipreps were prepared to confirm the expression of the recombinant protein.

Sufficient γ-glutamylcysteine synthetase was purified from E. coli BL21 (DE3) by nickel-NTA affinity chromatography, using the procedure described in Example 7 for purification of pAC2-1 T. vaginalis homocysteinase.

part B—Assay Methodology using γ-glutamylcysteine Synthetase and $Zn(OH)_2$ Trapping According to the practice of the invention, following use of γ-glutamylcysteine synthetase to deplete cysteine from a biological sample, determination of the homocysteine concentration therein may then be accomplished by any of several procedures, preferably those involving use of a homocysteinase, with detection of one or more resulting reaction products.

A further example of an effective assay procedure is presented below, and involves colorimetric detection of methylene blue which is itself produced, in situ, in a reaction that efficiently consumes the hydrogen sulfide produced in the homocysteinase reaction. This procedure takes advantage of the efficient detection of the dye molecule methylene blue (methyl thionine chloride) in the visible range, such as at 740 nm. Specifically, methylene blue is produced by oxidation of N,N-dimethyl-p-phenylenediamine ("NDPD") with ferric chloride in the presence of hydrogen sulfide. In a variation on this reaction scheme, N,N-diethyl-p-phenylenediamine is substituted for N,N-dimethyl-p-phenylenediamine, with the result that chromophoric detection is enhanced, by up to about 5-fold. As will be recognized in the art, other sources of ferric iron are suitable.

While in view of the present disclosure, those skilled in the art will recognize that numerous methods are available to detect sample homocysteine, this "methylene blue procedure" has been found to be particularly useful in a clinicial setting where rapid, accurate, and economical screening of a large number of samples is required.

Procedures demonstrating the method were performed as follows. A sample of human serum was diluted (1:1) with phosphate buffered saline, and then deproteinized by ultra-filitration using an Amicon 30k Centriprep, with centrifugation at 4,000 rpm for 60 minutes at 4° C. The deproteinized and diluted serum was then collected and divided into 1 ml aliquots in Eppendorf tubes for use in the assays. In the below-described procedures, free homocysteine was determined. That fraction of total serum homocysteine that is present as a disulfide dimer (homocystine or cysteine/homocysteine heterodimer), or is found disulfide-bonded to protein, may also be determined by including a reducing step (for example, addition of 5 mM β-mercaptoethanol) at an appropriate point in the protocol. However, in view of the capacity of such agents to inactivate proteins (including γ-glutamylcysteine synthetase and homocysteinases), it is preferable to select as reducing agent (see below) a specialized compound capable of reducing the disulfide bond of homocystine, for example, without inactivating γ-glutamylcysteine synthetase or homocysteinase.

In these protocols, validations were first performed to confirm assay reproducibility. Accordingly, in a first test, separate tubes of serum (1:1 diluted and deproteinized) were spiked with different amounts of homocysteine (to attain final concentrations of 1 μM, 5 μM, 10 μM, 15 μM, and 20 μM). A 50 μl aliquot of homocysteinase (either the Trichomonas vaginalis enzyme expressed from pAC2-1, SEQ ID NO: 10, or wild type Pseudomonas pudita enzyme), was then added to each tube, and each tube was incubated at 37° C. for 20 minutes with the lid tightly closed (to retain $H_2S$). The reaction was stopped by addition of 100 μl of 1 M NaOH, with mixing, followed immediately by a further addition of 0.3 ml of trapping solution (solution A), rapid mixing, and then centrifugation at 13,000 rpm for 1 minute (solution A was made by dissolving 4 g NaOH, 2.94 g trisodium citrate, and 10 g zinc acetate in 1 liter of water). The supernatant in each tube was then discarded, and the pellets were dissolved in 0.15 ml of solution B (2.7% w/v $FeCl_3$ in 6N HCl) followed by addition of 0.75 ml solution C (0.2% w/v NDPD in 1N HCl). The contents were mixed thoroughly, followed by incubation at room temperature for 30 minutes, again with the lids closed. The concentration of product methylene blue, which is reflective of $H_2S$ produced in the homocysteinase reaction, was read at 740 nm in a spectrophotometer. Linearity of the result was good for both the recombinant Pseudomonas putida and Trichomonas vaginalis enzymes.

A similar set of assays was performed in which serum was spiked to achieve a cysteine concentration of between 1 and 20 micromolar. In comparing the outcome for a recombinantly produced Trichomonas vaginalis enzyme (SEQ ID NO:10, from clone pAC2-1) and a recombinantly produced wild type Pseudomonas pudita enzyme, the experiment demonstrated that in spite of the high activities both enzymes show toward homocysteine, the pAC2-1 variant has much less activity toward cysteine and is therefore preferred.

The following procedure demonstrates the use of the preferred combination of Trichomonas vaginalis enzyme from clone pAC2-1, and γ-glutamylcysteine synthetase from E. coli B.

In an example of the assay, in a sealable Eppendorf tube an incubation mixture (1 ml) was prepared to contain 10 mM in L-glutamate, 2 mM ATP, 25 mM $MgCl_2$, buffered with Tris-Cl, 100 mM at pH. 8.0, and included 5 μg recombinant γ-glutamylcysteine synthetase from clone GSH-I His, and a sufficient amount of the biological sample to deliver, for example, about 50 μmoles of homocysteine. Note also that it is prefered to add the reagents to the tube in the following order, from the following stock solutions:

(1) 700 μl of water;
(2) 100 μl of 1M Tris pH 8.0;

(3) homocysteine/cysteine-containing sample (about 50 μl), or other amount as appropriate;
(4) 100 μl of 100 mM L-glutamate;
(5) 20 μl of 100 mM ATP;
(6) 10 μl of 2.5 M $MgCl_2$; and
(7) 10 μl of 0.5 mg/ml recombinant γ-glutamylcysteine synthetase from clone GSH-I His.

The contents are incubated at 25° C. for 30 minutes, after which 10 μl of homocysteinase enzyme (4.5 mg/ml of *Trichomonas vaginalis* enzyme, SEQ ID NO:10, from clone pAC2-1) is added, the vial sealed, followed by a further incubation at 37° C. for 20 minutes. Production of $H_2S$ is stopped by addition of 100 μl of 1M NaOH, with mixing, followed by 300 μl of solution A, with mixing, after which the tube is spun at 13,000 rpm for 45 seconds as above. Following careful removal of all of the supernatant, the pellet is resuspended in 150 μl solution B, followed by addition of 750 μl of solution C and a further 20 minute incubation period at room temperature. Methlyene blue production is monitored within the visible range, most preferably from about 650 to 750 nm.

It is noted that although literature reports indicate that γ-glutamylcysteine synthetase may function optimally around 45 degrees C, in the practice of the present invention it has been found to work quite well at 25 degrees C.

As previously mentioned (see Example 4), a significant fraction of homocysteine that is present in biological samples may be bonded to other biological molecules, and such "stored" forms of homocysteine are believed to contribute to pathological processes. Thus, in determining homocysteine concentrations, it is desireable to include these other forms. Major contributors to the total homocysteine concentration include (1) homocysteine dimers, (2) homocysteine/cysteine heterodimers, and (3) conjugates of homocysteine and protein wherein homocystiene is attached by way of a disulfide bond to protein cysteine. According to the practice of the present invention, the total of such additional homocysteine concentrations may be accurately determined by appropriate use of a disulfide bond reducing agent. Not all disulfide reducing agents are particularly suitable for this function since they also present the capacity to reduce disulfide bonds in homocysteinases or γ-glutamylcysteine synthetases, participate in thiol exchange reactions, or react directly with enzyme thiol groups, thereby altering the activity of the enzymes. One such less preferred agent is β-mercaptoethanol.

A disulfide reducing agent that is potentially useful in the practice of the invention is tris-(2-carboxyethyl)phosphine ("TCEP"), available from Molecular Probes Inc., Eugene, Oreg. which may be prepared fresh as a 100 mM stock solution (for use at 10 μl/1 ml tube sample) and which may be preferably dispensed into the vial just prior to addition of the homocysteine-containing biological sample itself. Additional suitable reducing agents will be recognized by those familiar with the art. In fact, DTT has been found to be the most preferred reducing agent, and causes minimal effects on assay enzymes.

This aspect of the invention is represented by a method for determining the amount of homocysteine that is present in a biological sample containing homocysteine and cysteine, which method comprises measuring the concentration of a product that is produced from homocysteine in a reaction catalyzed by a homocysteinase, which product may also be produced by reaction of said homocysteinase upon cysteine in said sample, and wherein said sample contains an otherwise interfering concentration of cysteine, said method comprising the steps of:

(a) incubating said sample with γ-glutamylcysteine synthetase in the presence of substrates that permit conversion of cysteine to γ-glutamylcysteine;
(b) incubating the mixture resultant from step (a) with homocysteinase; and
(c) measuring the concentration of a product that is capable of being produced from both homocysteine and cysteine in a reaction catalyzed by a homocysteinase, wherein said step of making disulfide bonded homocysteine molecules available for reaction with homocysteinase is performed by treating said sample with tris-(2-carboxyethyl) phosphine at a point prior to step (a) thereof.

Alternate Procedure Involving Detection of Product Ammonia

As aforementioned, the ammonia product of the homocysteinase reaction may also be used to quantify homocysteine in biological samples. However, in addition to interference caused by concentrations of cysteine (which is addressed appropriately according to the above-described procedures), interference by methionine is possible if ammonia is being detected. In this case, correction may be accomplished generally by recognizing that methionine can also be detected by release of methanethiol during the homocysteinase reaction itself. Thus, its concentration may be measured and then substracted. The resultant methanethiol can be determined by production of methylene blue (including variants thereof) by measuring OD at about 510 nm, using as reactant N,N-dimethyl [or diethyl]-p-phenylenediamine. See Tanaka et al., *Journal of Applied Biochemistry*, 2, pp. 439–444, 1980. Ammonia, as is recognized in the art, may also be measured in assays that involve glutamate dehydrogenase, and such procedures may be adapted to the practice of the present invention.

Example 11

An Enhanced Detection Procedure for Hydrogen Sulfide

An enhanced methodology for the detection of hydrogen sulfide has been developed which is related to that presented in Example 10 above. Diagnostic kits according to this aspect of the invention are prepared as follows.

The following reagents/stock solutions are prepared:
(a) buffer solution—a stock solution of 50 mM borate buffer, pH 7.5, prepared from 309 mg $H_3BO_3$, f.w.61.83, added to 90 ml dd water, the pH is adjusted to 7.5 with NaOH, after which the volume is brought up to a total of 100 ml with dd water. Any acceptable buffer can be used in place of the borate buffer used in this example, such as sodium phosphate buffer and tris buffer.
(b) reducing agent—15.4 mg DL-dithiothreitol ("DTT"), Sigma, St. Louis, Mo., is dissolved in 1 ml of borate buffer(a) resulting in a 100 mM solution. Any acceptable reducing agent can be used in place of the DTT used in this example, such as TCEP (tris(2-carboethyl)phosphine) and β-mercapto ethanol.
(c) chromogenic reagent I—33.25 mg of potassium ferricyanate, $K_3Fe(CN)_6$, Sigma, is dissolved in a solution of 10 ml of 1N HCl, 1% (w/v) Triton X-100, Sigma, creating a 10 mM stock solution of ferric iron. This solution should be mixed well before use. Other acceptable surfactants, other than the Triton X-100 surfactant, can also be used.
(d) chromogenic reagent II—52.5 mg of N,N-dipropylphenylene diamine ("DPPDA"), Wako Pure Chemical Industries, Ltd., Japan, is dissolved in dd water up to a final concentration of 100 mM.

(e) recombinant homocysteinase—the enzyme represented by SEQ ID NO:10 (derived from *E. coli* clone pAC2-1, ATCC 98549) may be purchased as product HYase™ from AntiCancer, Inc, San Diego, Calif. and has a molecular weight of 172,000 and a specific activity of 40 units/mg. The enzyme should be diluted to 4 units/ml with borate buffer before use, stored during assays at 0–4° C., and prepared fresh for each use.

(f) DL-homocysteine—2.7 mg of DL-homocysteine, Sigma, is added to 2 ml borate buffer (4 mM final concentration), and prepared fresh daily as a calibration standard, with storage during use at 0–4° C. (Note: in general homocysteinases use only the natural L-optical isomer of homocysteine, but the D/L mixture provides an economical source of of the L-isomer, requiring of course use of a correction factor of 50% to provide the effective L-concentration).

A representative assay protocol is as follows. 0.1 ml of blood plasma is added to 0.9 ml of borate buffer. 10 µl of the 100 mM DTT solution is then added, mixed well, followed by an incubation at 37° C. for 30 minutes. 30 µl of HYase™ recombinant homocysteinase (prediluted to 4 units/ml in borate buffer) is then added with mixing, followed by a further incubation period at 37° C. for 1 minute. 200 µl of chromogenic reagent I and 10 µl of chromogenic reagent II are then added simultaneously with mixing and the sample is incubated at 37° C. for 20 minutes. The product methylene blue-type chromophore is then detected by measuring the OD at 677 nm in a spectrophotometer. The plasma concentration of L-homocysteine is then determined from a constructed calibration curve, which may use homocysteine and/or the disulfide bonded dimer thereof, homocystine, as standards. In providing this representative example, it is of course apparent that considerable variation in the selection of assay reagents or reagent concentrations is possible, and such modifications will be recognized immediately as within the skill of art.

Example 12

Additional Methodology

The following provides additional examples of procedures, and variations thereof, which the practitioner may find useful in the practice of the invention.

Growth of Recombinant Bacteria

Each fermentation run was started with one vial of recombinant *E. coli* containing recombinant homocysteinase (pAC2-1, see SEQ ID NOS: 9 and 10) from the master cell bank (MCB). Ten microliters of bacteria from the MCB were seeded into 5 ml LB medium and grown overnight at 37° C. with shaking at 400 rpm. The culture was transferred to 800 ml LB medium in 6 L flasks and grown overnight at 37° C. at 400 rpm at which time the $OD_{600}$ was approximately 10. The bacteria were collected by centrifugation at 4000 rpm for 20 min. The bacteria were then transferred into 800-ml LB-medium cultures in 6 L flasks and grown at 37° C. at 400 rpm for 16 h. The bacteria were harvested by centrifugation at 4000 rpm at 4° C. for 20 minutes.

Precolumn Treatment

The bacterial pellets, derived from 90×800-ml cultures of recombinant *E. coli*, were combined and disrupted with a cavitation type homogenizer (Microfluidics Corp., Newton, Mass.; model HC 8000). The homogenate was suspended in 2 vol. of 20 mM potassium phosphate pH 7.2 containing 10 µM pyridoxal phosphate, 0.01% β-mercaptoethanol and 20% ethanol. Heat treatment of the homogenate was carried out at 50° C. for 1 minute. 1% (w/v) polyethyleneimine (PEI) was added to the suspension solution and mixed for 20 minutes. The suspension was centrifuged with an automatic refrigerated centrifuge (Sorvall, Superspeed RC 2-B) at 4° C. at 12,000 rpm for 40 minutes to remove nucleic acids. The supernatant was then collected and mixed with polyethylene glycol 8000 (PEG 8000) to a final concentration of 10–12% (w/v) and stirred at 4° C. for 60 minutes. The precipitate (containing contaminating proteins) was removed by centrifugation at 12,000 rpm for 40 minutes. 3.0 M sodium chloride was then added to the supernatant to give a final concentration of 0.12 M which precipitated recombinant homocysteinase. The pellet was collected by centrifugation at 12,000 rpm for 40 minutes and dissolved in 20 mM potassium phosphate buffer pH 7.6, containing 10 µM pyridoxal phosphate and 0.01% β-mercaptoethanol.

DEAE-Sepharose FF Chromatography

The enzyme sample from the precolumn treatment was applied to a column of DEAE-Sepharose FF (30×5 cm) (Pharmacia) that was previously equilibrated with 20 mM potassium phosphate pH 7.2. After loading the column, it was prewashed with 50 mM sodium chloride, 20 mM potassium phosphate pH 7.2 for approximately 3 volumes, until the $OD_{280}$ dropped below 0.1. Recombinant homocysteinase was then eluted with a linear sodium chloride concentration gradient of 0.05–0.5 M in the same buffer over 90 minutes.

Phenyl-Sepharose 6 FF Chromatography

Solid ammonium sulfate (79.3 mg/ml) was added to the active fractions of the DEAE-Sepharose FF chromatography to give a final concentration of 0.6 M. Before loading the supernatant on the Phenyl-Sepharose 6 FF column (20×2.6 cm), the column was equilibrated with Buffer A—consisting of 0.6 M ammonium sulfate in 20 mM potassium phosphate pH 7.6. Bound protein was eluted by linearly decreasing the ammonium sulfate gradient with Buffer B (which contained 20 mM potassium phosphate pH 7.6, 10 µM pyridoxal phosphate, 0.02% β-mercaptoethanol, and 5.0% ethylene glycol). The active fractions were concentrated by DEAE-Sepharose FF (20×1.6 cm) which removed ammonium sulfate and polyethylene glycol. Purified enzyme was stored at −80° C.

Activity Assays for Recombinant Homocysteinase

An activity assay for the keto product of the α, γ or α,β-elimination (alpha keto butyrate for homocysteine) was carried out in in a 1.5 ml Eppindorf tube using 1-ml. of 50 mM phosphate buffer pH 8.0 (also containing 10 µM pyridoxal phosphate and 20 mM homocysteine) for 10 minutes at 37° C., with varying amounts of enzyme. The reaction was stopped by adding 0.5 ml of 4.5% TCA. 0.05 ml of the resultant solution was then combined with 0.45 ml of 0.05% 3-methyl-2-benzothiazothiazolinone hydrazone (MBTH) and added to a 1.0 ml sample of 1.0 M sodium acetate, pH 5.2, followed by incubation at 50° C. for 30 minutes.

The amount of reaction product was determined by spectrophotometry at $OD_{335}$. The hydrazone product has an extinction coefficient of $7.6 \times 10^3$ l/mol×cm. The amount of protein was determined with the Lowry Reagent Kit (Sigma) with bovine serum albumin as a standard. The specific activity was calculated as units/mg protein, with one unit of enzyme defined as the amount that catalyzed the formation of 1 µmol of α-ketobutyrate/minute.

Activity assays for the γ and β elimination reactions of homocysteine and cysteine, respectively, were carried out at 37° C. for 30 seconds. The resulting $H_2S$ produced was measured using methylene blue formation at $OD_{671}$.

SDS-PAGE and PAGE

Electrophoresis was performed according to the methods described in the NOVEX Kit (NOVEX Experimental Technology, San Diego). A 12% Tris-Gel was used for SDS-PAGE. After staining with Coomassie brilliant blue, the intensity of protein bands was estimated with molecular standards (NOVEX mark 12 Wide Range Protein Standard), including myosin, 200 kD; β-galactosidase, 116.3 kD; phosphorylase b, 97.4 kD; bovine serum albumin, 66.3 kD; carbonic anhydrase, 31.0 kD; trypsin inhibitor, 21.5 kD; lysozyme, 14.4 kD; aprotinin, 6.0 kD. Native gels were stained for recombinant homocysteinase activity by immersion in a reaction mixture containing 3.3 mM-DL-homocysteine, 0.33 mM lead acetate, 28.4 mM β-mercaptoethanol, and 100 mM Tris-HCl buffer, pH 7.5. Bands containing homocysteinase activity will convert homocysteine to α-ketobutyrate, ammonia and $H_2S$. Hydrogen sulfide reacts with lead acetate to form a dark brown precipitate ($Pb_2S$). The gels were then stained for protein with Coomassie Blue.

Example 13

A Fluorescence-Based Homocysteine Diagnostic Assay

By using fluorescence to determine the concentration of the resulting chromophore in a homocysteine assay, the sensitivity can be enhanced approximately 1000-fold in comparison to the sensitivity using absorbance. Therefore, smaller samples, about 10 to 100 fold smaller, can be analyzed using the more sensitive fluorescence-based determination than the absorbance-based determination described above. For example a blood sample derived from finger pricking is sufficient to achieve a strong fluorescence signal in the homocysteine assay.

Figure 6:
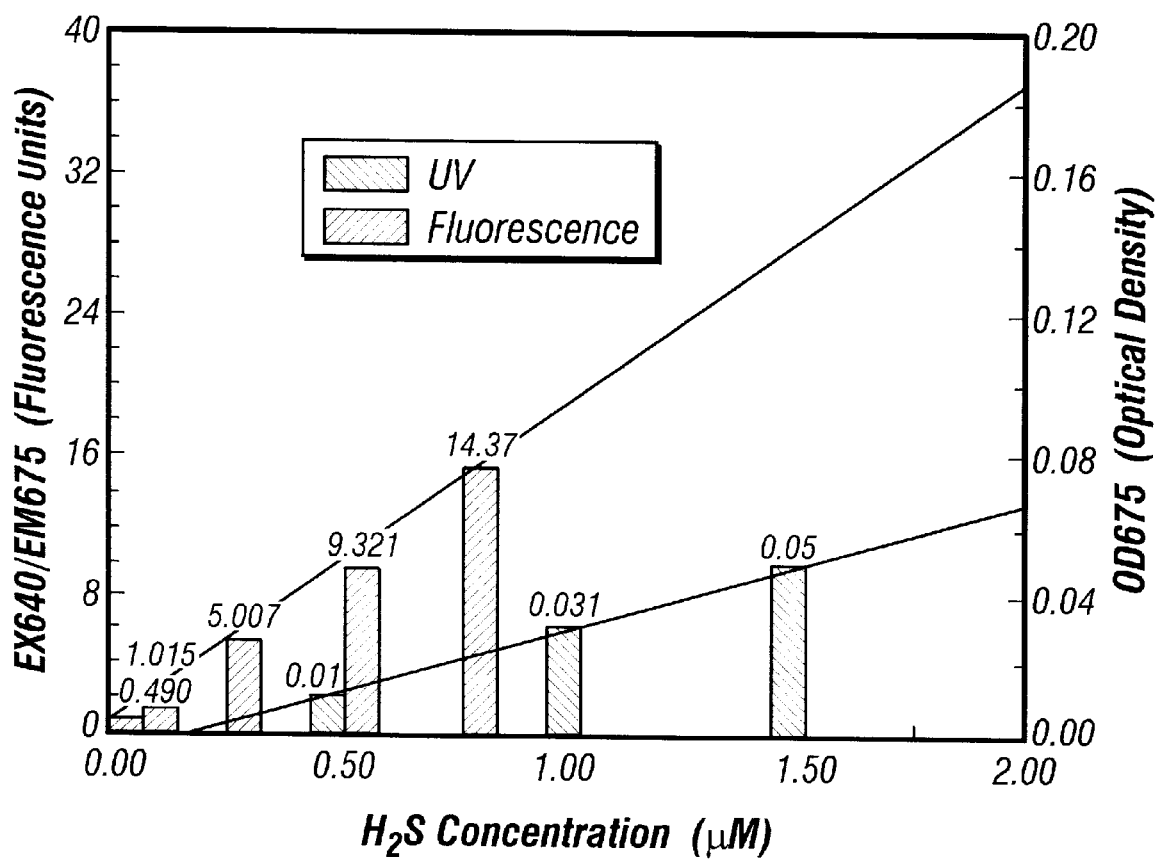
FIG. 6 provides a comparison of fluorescence and ultraviolet absorption at various hydrogen sulfide concentrations.

The increased sensitivity of the fluorescence-based assay in comparison to the absorbance-based assay is shown in FIG. 6. In this figure, the X axis represents the hydrogen sulfide concentration in the assay. The steeper curve for the fluorescence signal than for the absorbance signal for the same assay having varying concentrations demonstrates that the fluorescence signal is much more sensitive than the absorbance signal.

Any suitable reagent that provides a proper signal when measured by fluorescence is appropriate. For example, the chromogenic reagent, N,N-dibutyl-phenylene-diamine (DBPDA), used for absorbance as discussed above was used in the fluorescence-based assay illustrated in FIG. 6. Generally, the same conditions used for the absorbance-based assays can be used for the fluorescence-based assays, except the assays are measured by fluorescence.

A very strong signal by fluorescence can be obtained using an appropriate combination of excitation and emission wavelengths, which can be determined by one having ordinary skill in the art. For example, excitation at 665 nm and emission at 690 nm, or excitation at 640 nm and emission at 675 can be used under certain conditions.

Figure 7:
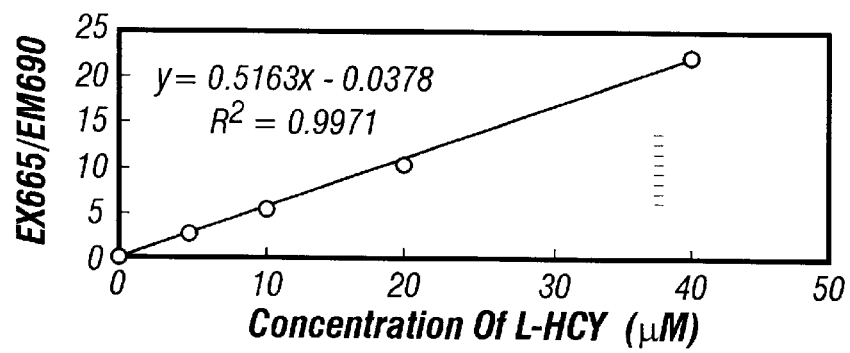
FIG. 7 shows the standard curve of L-homocysteine.
Figure 8:
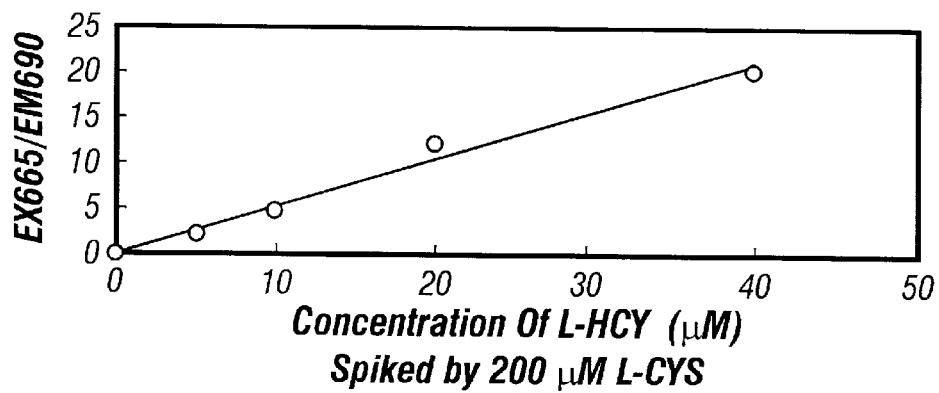
FIG. 8 shows a curve of homocysteine demonstrating the relative lack of interference by cysteine in an enzymatic homocysteine assay measured by fluorescence and results of a blood sample derived from finger pricking.
Figure 9:
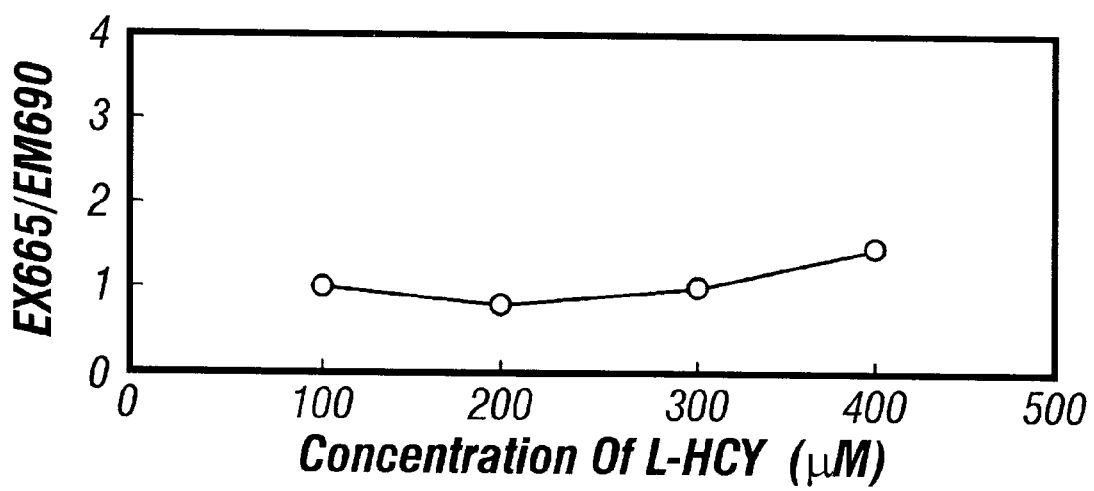
FIG. 9 shows the interference of cysteine measured by fluorescence at various concentrations of cysteine.

A comparison of FIG. 7's standard curve for homocysteine, based on measurements by fluorescence, and FIG. 8's curve for homocysteine samples that also contain a fixed amount of cysteine, shows that cysteine has minimal interference with the homocysteine measurement. These results are consistent with absorbance-based assays. FIG. 9 shows the interference by cysteine samples of varying concentrations.

A small sample of blood derived from finger pricking was used to determine the homocysteine concentration therein. Corresponding the fluorescence readout of the sample with the appropriate concentration in the standard curve in FIG. 7 gave the concentration shown in the results in the chart in FIG. 7.

In further support of the present disclosure, on Sep. 26, 1997, a deposit of biological material of confirmed viability was made with the American Type Culture Collection, Rockville, Md., USA under the Budapest Treaty. The material is identified as *E. coli* BL21 (DE3), clone pAC2-1, and has been assigned ATCC number 98549. Upon the granting of a patent herein, all restrictions on the availability of this material to the public will be irrevocably removed.

What is claimed is:

1. A diagnostic kit for use in a single enzyme assay of the homocysteine concentration in a biological fluid of a subject, said kit comprising:
   (a) a homocysteinase enzyme; and
   (b) at least one reagent capable of being used to determine by fluorescence the amount of product hydrogen sulfide formed by reaction of homocysteinase on homocysteine; wherein
      said homocysteinase is sufficiently non-reactive toward cysteine that any hydrogen sulfide produced by reaction of said homocysteinase on cysteine does not substantially interfere with the use of said kit to assess risk for cardiovascular disease.

2. The diagnostic kit of claim 1 wherein the homocysteinase included therein has the property that at least about 90% of the hydrogen sulfide produced by action of said homocysteinase upon contacting a biological fluid in an assay for homocysteine is contributed by said homocysteine, when the concentrations of homocysteine and cysteine in said fluid are, respectively, about 5–15 μmolar and about 100–300 μmolar respectively.

3. The diagnostic kit of claim 1 wherein said homocysteinase included therein has the property that at least about 99% of the hydrogen sulfide produced by action of said homocysteinase upon contacting said biological fluid in an assay for homocysteine is contributed by said homocysteine.

4. The diagnostic kit of claim 1 capable of being used to determine a homocysteine concentration in said biological fluid in the range of 1–500 μmolar, wherein said fluid also contains about 10 to about 1000 μmolar of cysteine.

5. The diagnostic kit of claim 1 capable of being used to determine the homocysteine concentration in tissue fluid, blood, blood plasma, blood serum or urine.

6. The diagnostic kit of claim 1 further comprising one or more reagents selected from the group consisting of:
   (a) an agent capable of reducing disulfide bonds;
   (b) a source of ferric iron;
   (c) an N,N-dialkyl-p-phenylene diamine; and
   (d) homocysteine as a calibration standard.

7. The diagnostic kit of claim 1 comprising:
   (a) SEQ ID NO: 10, or residues $Met^1$ through $Leu^{396}$ thereof, as homocysteinase in a concentration of 0.01–1000 μM/ml;
   (b) at least one buffer having a concentration of 10 mM–1 M and a pH of 7–9.5 selected from the group consisting of sodium phosphate buffer, tris buffer and borate buffer; and at least one reducing agent having a concentration of 0.1 mM–1 M selected from the group consisting of DL-dithiothreitol, TCEP, and β-mercaptoethanol; 0.01–100 mM potassium ferricyanate, 0.1–10% w/v surfactant (detergent); a 0.01–100 mM solution of N,N-dialkyl-phenylene diamine having a dialkyl group selected from the group consisting of dimethyl, diethyl, dipropyl and dibutyl; and (c) homocysteine and/or homocystine as a calibration standard.

8. In a method for determining the amount of homocysteine present in a biological fluid of a subject wherein said method comprises the step of contacting said sample with an enzyme capable of catalyzing production from homocysteine of a detectable quantity of hydrogen sulfide, and wherein said sample further comprises an amount of cysteine from which a detectable quantity of hydrogen sulfide can be produced that interferes with said determination, the improvement comprising selecting, for use therein, a homocysteinase having the property that at least about 90% of the hydrogen sulfide produced by action of said homocysteinase upon contacting said biological fluid therewith, in an assay for homocysteine, is contributed by said homocysteine, when the concentrations of homocysteine and cysteine in said fluid are, respectively, about 1–500 μmolar and about 10–1000 μmolar respectively, and measuring by fluorescence the amount of product hydrogen sulfide formed.

9. A single enzyme method for determining the concentration of homocysteine in a biological fluid of a subject that comprises use of a diagnostic kit according to claim 1.

10. A diagnostic method to assess risk for cardiovascular disease in a subject, wherein the concentration of homocysteine in a biological fluid of said subject is determined, absent interference from concentrations of cysteine and methionine in said fluid, said method comprising the steps of:

(a) contacting the biological fluid sample with an agent capable of reducing disulfide bonds in order to liberate as free homocysteine that fraction of total homocysteine present therein in disulfide-bonded form;

(b) contacting said sample with a homocysteinase that is substantially non-reactive to cysteine compared to homocysteine, such that at least about 90% of the hydrogen sulfide produced by said contacting is produced from homocysteine, under conditions where said hydrogen sulfide does not escape;

(c) adding ferric iron and an N,N-dialkyl-phenylene diamine to said hydrogen sulfide-containing sample in order to produce, in situ, a methylene blue-type chromophore;

(d) determining by fluorescence the concentration of homocysteine that was present in said sample based on the concentration of chromophore produced; and (e) comparing said result to levels of homocysteine in biological fluids of subjects that are known to correlate with increased risk for cardiovascular disease.

11. The method of claim 10 wherein said homocysteinase is SEQ ID NO: 10, or residues $Met^1$ through $Leu^{396}$ thereof.

12. The method of claim 10 wherein said biological fluid sample is selected from the group consisting of tissue fluid, urine, blood, blood serum, and blood plasma.

13. The diagnostic kit of claim 1 comprising:

(a) a homocysteinase that is substantially non-reactive to cysteine compared to homocysteine;

(b) a buffer, a reducing agent, an agent useful to detect hydrogen sulfide by fluorescence; and optionally, (c) homocysteine and/or homocystine as a calibration standard.

14. The diagnostic kit defined in claim 7 wherein the buffer is sodium phosphate having a pH of about 8.3, the reducing agent is DL-dithiothreitol, and the N,N-dialkyl-phenylene diamine is N,N-dibutyl-phenylene diamine.

15. In a method for determining the amount of homocysteine present in a sample of biological fluid of a subject containing 1–1000 μM homocysteine using the diagnostic kit of claim 7, wherein said method comprises the step of contacting said sample with an enzyme capable of catalyzing production from homocysteine of a detectable quantity of hydrogen sulfide, and wherein said sample further comprises an amount of cysteine from which a detectable quantity of hydrogen sulfide can be produced that interferes with said determination, the improvement comprising selecting, for use therein, a homocysteinase having the property that at least about 90% of the hydrogen sulfide produced by action of said homocysteinase upon contacting said biological fluid therewith, in an assay for homocysteine, is contributed by said homocysteine, when the concentrations of homocysteine and cysteine in said fluid are, respectively, about 1 to about 500 μmolar and about 10 to about 1000 μmolar respectively, and measuring by fluorescence the amount of product hydrogen sulfide formed;

wherein homocysteinase is added to said sample in an amount needed to achieve a final concentration of 0.01–1000 μg/ml; and wherein reagents are added in amounts needed to achieve final concentrations of 1–100 mM of buffer; 0.01–100 mM reducing agent; 0.01–10 mM potassium ferricyanate, 0.01–1.0% w/v surfactant; and about 0.01–10 mM solution of N,N-dialkyl-phenylene diamine.

16. The method defined in claim 15 wherein homocysteinase is added in an amount needed to achieve a final concentration of about 1 μg/ml; and wherein the buffer is sodium phosphate added in an amount needed to achieve a final concentration of about 10 mM, the reducing agent is DL-dithiothreitol added in an amount needed to achieve a final concentration of about 0.5 mM, and the N,N-dialkyl-phenylene diamine is N,N-dibutyl-phenylene diamine added in an amount needed to achieve a final concentration of about 0.5 mM, and wherein potassium ferricyanate and the surfactant are added in amounts needed to achieve final concentrations of about 0.25 mM and 0.1% w/v, respectively.

17. A method of using the diagnostic kit defined in claim 7 to assess risk for cardiovascular disease in a subject, wherein a concentration of a subject's biological fluid sample containing 1–1000 μM homocysteine is determined, absent interference from concentrations of cysteine and methionine in said fluid, said method comprising the steps of:

(a) adding to said sample said buffer in an amount needed to achieve a final concentration of 1–100 mM;

(b) contacting the buffered sample with reducing agent in an amount needed to achieve a final concentration of 0.01–100 mM reducing agent, wherein said reducing agent is capable of reducing disulfide bonds in order to liberate as free homocysteine that fraction of total homocysteine present therein in disulfide-bonded form;

(c) contacting said sample containing the reducing agent with homocysteinase, in an amount needed to achieve a final concentration of 0.01–1000 μg/ml homocysteinase, wherein said homocysteinase is substantially non-reactive to cysteine compared to homocysteine, such that at least about 90% of the hydrogen sulfide produced by said contacting is produced from homocysteine, under conditions where said hydrogen sulfide does not escape;

(d) adding potassium ferricyanate and surfactant, in an amount needed to achieve a final concentration of 0.01–10 mM of potassium ferricyanate, 0.01–1% (w/v) of surfactant, and N,N-dialkyl-phenylene diamine in an amount needed to achieve a final concentration of 0.01–10 mM, to said hydrogen sulfide-containing sample in order to produce, in situ, a methylene blue-type chromophore;

(e) determining by fluorescence the concentration of homocysteine that was present in said sample based on the concentration of chromophore produced; and (f) comparing said result to levels of homocysteine in biological fluids of subjects that are known to correlate with increased risk for cardiovascular disease.

18. The method defined in claim 17 wherein homocysteinase is added in an amount needed to achieve a final concentration of about 1 μg/ml; and wherein the buffer is sodium phosphate added in an amount needed to achieve a final concentration of about 10 mM, the reducing agent is DL-dithiothreitol added in an amount needed to achieve a final concentration of about 0.5 mM, and the N,N-dialkyl-phenylene diamine is N,N-dibutyl-phenylene diamine added in an amount needed to achieve a final concentration of about 0.5 mM, and wherein reagents are added in amounts needed to achieve final concentrations of about 0.25 mM potassium ferricyanate and about 0.1% (w/v) surfactant.

19. A single enzyme method for determining the concentration of homocysteine in a biological fluid of a subject that comprises use of a diagnostic kit according to claim 7.

* * * * *